(12) United States Patent
Thomas et al.

(10) Patent No.: US 12,239,852 B2
(45) Date of Patent: Mar. 4, 2025

(54) MOTION SYNCHRONIZED ARC RADIOTHERAPY

(71) Applicant: PROVINCIAL HEALTH SERVICES AUTHORITY, Vancouver (CA)

(72) Inventors: Steven Thomas, Vancouver (CA); Kirpal Kohli, Surrey (CA); Justin Jeremy Jeun-Ming Poon, Vancouver (CA)

(73) Assignee: Steven Thomas, et al., Vancouver (CA)

( * ) Notice: Subject to any disclaimer, the term of this patent is extended or adjusted under 35 U.S.C. 154(b) by 889 days.

(21) Appl. No.: 17/309,457

(22) PCT Filed: Nov. 28, 2019

(86) PCT No.: PCT/CA2019/051707
§ 371 (c)(1),
(2) Date: May 27, 2021

(87) PCT Pub. No.: WO2020/107121
PCT Pub. Date: Jun. 4, 2020

(65) Prior Publication Data
US 2021/0370097 A1 Dec. 2, 2021

Related U.S. Application Data

(60) Provisional application No. 62/772,276, filed on Nov. 28, 2018, provisional application No. 62/839,854, filed on Apr. 29, 2019.

(51) Int. Cl.
*A61N 5/10* (2006.01)

(52) U.S. Cl.
CPC ........... *A61N 5/1068* (2013.01); *A61N 5/103* (2013.01); *A61N 5/1037* (2013.01);
(Continued)

(58) Field of Classification Search
CPC ........ A61N 5/10; A61N 5/103; A61N 5/1031; A61N 5/1037; A61N 5/1042;
(Continued)

(56) References Cited

U.S. PATENT DOCUMENTS 6,279,579 B1 * 8/2001 Riaziat ................. A61N 5/1049
128/897
6,621,889 B1 * 9/2003 Mostafavi ............ A61N 5/1048
378/65

(Continued)

FOREIGN PATENT DOCUMENTS

AU    2010273945 B2    7/2013
WO    2012044715 A1    4/2012

OTHER PUBLICATIONS

Cuculich, P. S. et al., "Noninvasive Cardiac Radiation for Ablation of Ventricular Tachycardia", The New England Journal of Medicine 2017;377:2325-2336, Dec. 14, 2017.

(Continued)

*Primary Examiner* — Allen C. Ho
(74) *Attorney, Agent, or Firm* — Borden Ladner Gervais; Richard A. Johnson

(57) ABSTRACT

Apparatus and methods for planning and/or delivering radiation treatment and controlling a radiation delivery system are described. Apparatus for delivering radiation treatment includes a radiation source, a drive connected to move the radiation source along a trajectory, a stored radiation treatment plan specifying a plurality of beam ON segments and beam OFF portions of the trajectory interleaved with the plurality of beam ON segments, and a monitor connected to detect progress of a physiological cycle of the patient, the physiological cycle has cycles that include quiescent periods. One or more data processors are connected to control the drive to advance the radiation source along the trajectory, control the radiation source to deliver radiation in each of the (Continued)

plurality of beam ON segments of the trajectory and to deliver no or negligible radiation in each of the beam OFF portions of the trajectory, process an output of the monitor to estimate a time for a next one of the quiescent periods, and control a speed at which the radiation source is advanced along the trajectory to cause the radiation source to arrive at a start of a next one of the beam ON segments at a time that coincides with the next one of the quiescent periods.

21 Claims, 10 Drawing Sheets

(52) U.S. Cl.
CPC ......... *A61N 5/1045* (2013.01); *A61N 5/1047* (2013.01); *A61N 5/1049* (2013.01); *A61N 5/1065* (2013.01); *A61N 5/1081* (2013.01); *A61N 2005/1055* (2013.01); *A61N 2005/1061* (2013.01)

(58) Field of Classification Search
CPC .. A61N 5/1045; A61N 5/1047; A61N 5/1048; A61N 5/1049; A61N 2005/1051; A61N 2005/1055; A61N 2005/1058; A61N 2005/1059; A61N 2005/1061; A61N 2005/1062; A61N 5/1064; A61N 5/1065; A61N 5/1067; A61N 5/1068; A61N 5/1071; A61N 2005/1072; A61N 2005/1074; A61N 5/1081
USPC ............................................................ 378/65
See application file for complete search history.

(56) References Cited

U.S. PATENT DOCUMENTS

| | | | |
|---|---|---|---|
| 6,690,965 B1* | 2/2004 | Riaziat ................... | A61B 6/463 378/65 |
| 6,889,695 B2 | 5/2005 | Pankratov et al. | |
| 6,937,696 B1* | 8/2005 | Mostafavi .............. | A61B 6/541 378/65 |
| 6,973,202 B2* | 12/2005 | Mostafavi .............. | A61B 6/463 382/103 |
| 6,980,679 B2* | 12/2005 | Jeung .................... | A61B 5/4818 382/128 |
| 7,609,810 B2* | 10/2009 | Yi ........................ | A61N 5/1049 378/65 |
| 7,623,679 B2* | 11/2009 | West ..................... | G06V 10/255 382/128 |
| 7,645,276 B2 | 1/2010 | Pankratov et al. | |
| 7,711,087 B2* | 5/2010 | Mostafavi ............ | A61N 5/1049 378/65 |
| 7,880,154 B2* | 2/2011 | Otto ..................... | A61N 5/1082 378/65 |
| 7,906,770 B2* | 3/2011 | Otto ..................... | A61N 5/1047 378/65 |
| 7,953,204 B2* | 5/2011 | Sumanaweera ....... | A61N 5/1049 378/65 |
| 8,027,431 B2* | 9/2011 | Stahl ...................... | A61N 5/103 378/65 |
| 8,042,209 B2* | 10/2011 | D'Souza .............. | A61N 5/1049 5/610 |
| 8,229,068 B2* | 7/2012 | Lu ........................ | A61N 5/1049 378/65 |
| 8,229,071 B2* | 7/2012 | Stahl .................... | A61N 5/1049 378/65 |
| 8,238,519 B2 | 8/2012 | Bani-Hashemi | |
| 8,295,435 B2* | 10/2012 | Wang ................... | A61N 5/1082 378/65 |
| 8,315,691 B2 | 11/2012 | Sumanaweera et al. | |
| 8,331,532 B2* | 12/2012 | Nord ..................... | G21K 1/046 378/65 |
| 8,345,821 B2* | 1/2013 | Sumanaweera ........ | A61B 6/032 378/68 |
| 8,422,631 B2* | 4/2013 | Takahashi .............. | A61N 5/103 378/65 |
| 8,460,166 B2* | 6/2013 | Guckenburger ....... | A61N 5/103 600/1 |
| 8,696,658 B2 | 4/2014 | Pankratov et al. | |
| 8,747,382 B2* | 6/2014 | D'Souza ................ | G16H 50/30 604/500 |
| 8,767,917 B2* | 7/2014 | Ruchala ................. | G16H 50/50 378/65 |
| 8,784,290 B2 | 7/2014 | Sumanaweera et al. | |
| 8,788,020 B2* | 7/2014 | Mostafavi .............. | A61B 5/741 324/309 |
| 8,792,613 B2 | 7/2014 | Gardner et al. | |
| 8,805,481 B2 | 8/2014 | Sumanaweera et al. | |
| 8,824,630 B2* | 9/2014 | Maurer, Jr. ............ | G16H 20/30 378/68 |
| 8,858,414 B2* | 10/2014 | Cheng .................. | A61N 5/1047 378/65 |
| 9,205,279 B2 | 12/2015 | Sumanaweera et al. | |
| 9,320,916 B2 | 4/2016 | Sumanaweera et al. | |
| 9,504,850 B2* | 11/2016 | Zhang .................. | A61N 5/1049 |
| 9,504,853 B2 | 11/2016 | Sumanaweera et al. | |
| 9,737,730 B2 | 8/2017 | Cheng et al. | |
| 9,788,783 B2 | 10/2017 | Otto | |
| 10,279,196 B2* | 5/2019 | West ..................... | A61N 5/1031 |
| 11,071,877 B2* | 7/2021 | Zhou .................... | A61N 5/1045 |
| 11,160,537 B2* | 11/2021 | Bruder ................. | A61N 5/1049 |
| 11,364,393 B2* | 6/2022 | Nord .................... | A61N 5/1081 |
| 11,413,002 B2* | 8/2022 | Gagnon ................ | A61B 6/488 |
| 2005/0171396 A1 | 8/2005 | Pankratov et al. | |
| 2008/0177279 A1 | 7/2008 | Sumanaweera et al. | |
| 2008/0177280 A1 | 7/2008 | Adler et al. | |
| 2009/0257557 A1 | 10/2009 | Sumanaweera et al. | |
| 2010/0160775 A1 | 6/2010 | Pankratov et al. | |
| 2011/0166408 A1 | 7/2011 | Sumanaweera et al. | |
| 2012/0323233 A1 | 12/2012 | Maguire et al. | |
| 2013/0102896 A1 | 4/2013 | Sumanaweera et al. | |
| 2013/0131425 A1 | 5/2013 | Sumanaweera et al. | |
| 2015/0290472 A1 | 10/2015 | Maguire et al. | |
| 2016/0000409 A1 | 1/2016 | Bruder et al. | |

OTHER PUBLICATIONS

Kohli, K. et al., "Prototype development of an electrical impedance based simultaneous respiratory and cardiac monitoring system for gated radiotherapy", Biomedical Engineering Online Oct. 14, 2014;13(1)144.

Maguire, P. J. et al., "Cardiac Radiosurgery (CyberHeart TM) for Treatment of Arrhythmia: Physiologic and Histopathologic Correlation in the Porcine Model", Cureus Aug. 2, 2011;3(8).

Ipsen, S. et al., "Radiotherapy beyond cancer: Target localization in real-time MRI and treatment planning for cardiac radiosurgery", Medical Physics Dec. 1, 2014;41(12).

Shuman, W. P. et al., "Prospective Versus Retrospective ECG Gating for 64-Detector CT of the Coronary Arteries: Comparison of Image Quality and Patient Radiation Dose 1", Radiology Aug. 2008;248(2)431-437.

\* cited by examiner

FIG. 4 - PRIOR ART

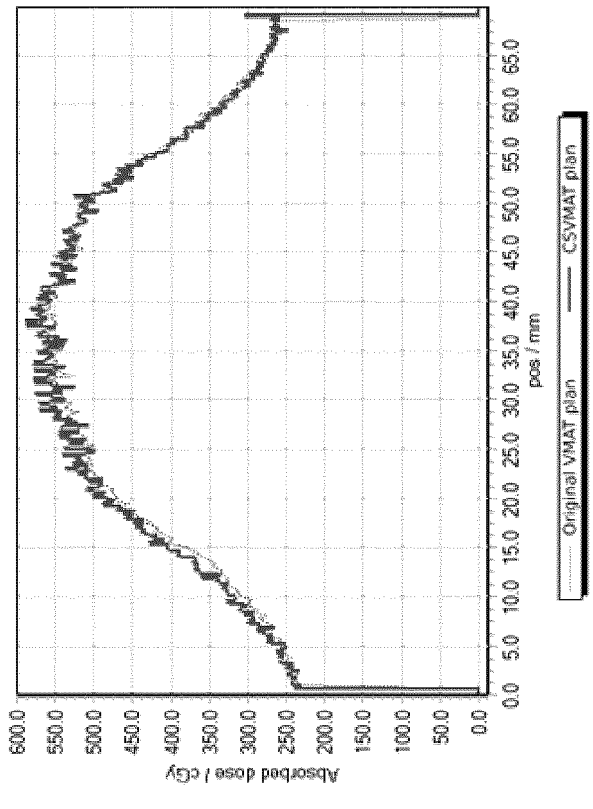
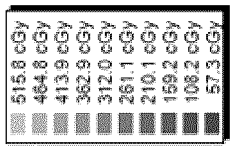
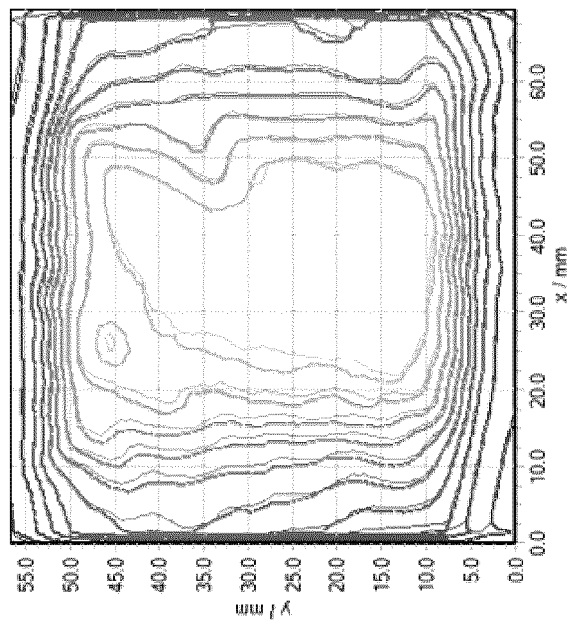
FIG. 7B
FIG. 7A

MOTION SYNCHRONIZED ARC RADIOTHERAPY

CROSS-REFERENCE TO RELATED APPLICATIONS

This application claims priority from U.S. patent application No. 62/772,276 filed 28 Nov. 2018 and from U.S. patent application No. 62/839,854 filed 29 Apr. 2019 which are hereby incorporated herein by reference for all purposes. For purposes of the United States, of America this application claims the benefit under 35 U.S.C. § 119 of U.S. application No. 62/772,276 filed 28 Nov. 2018 and entitled CARDIAC SYNCHRONIZED VOLUMETRIC MODULATED ARC THERAPY FOR CARDIAC STEREOTACTIC ABLATIVE RADIOTHERAPY which is hereby incorporated herein by reference for all purposes. This application also claims the benefit under 35 U.S.C. § 119 of U.S. application No. 62/839,854 filed 29 Apr. 2019 and entitled RESPIRATORY MOTION TRACKING VIA PATIENT INTERNAL FIDUCIALS which is hereby incorporated herein by reference for all purposes.

FIELD

This application relates to radiotherapy. Specific embodiments provide methods and apparatus for planning and/or delivering radiotherapy.

BACKGROUND

Radiotherapy involves delivering radiation to treat tissues. When radiation is prescribed for a particular target volume of tissue it would be ideal to deliver the prescribed dose of radiation to the target volume and to deliver zero radiation everywhere outside of the target volume. This is impossible when the radiotherapy is delivered by directing a beam of penetrating radiation from outside the body to irradiate the target volume. When this is done, radiation dose is delivered to the tissues that the radiation beam passes through before reaching the target volume as well as tissues that the radiation beam passes through after passing through the target volume. Radiation dose is also delivered to tissues outside of the beam as a result of scattering. Radiation dose may also be delivered to tissues outside of the target volume in cases where the radiation beam cannot be accurately shaped to conform to the target volume.

Various techniques have been developed to reduce the dose of radiation delivered to tissues outside a target volume. One approach involves irradiating the target volume from a range of different directions. This approach limits the dose of radiation delivered to tissues outside of the target volume by delivering radiation dose to the target volume from all of the directions but only delivering significant radiation dose to any specific volume of tissue outside of the target volume from some of the directions, thereby sparing the tissue outside of the target volume.

Radiation treatment planning is the process of designing a protocol for delivering a prescribed radiation dose to one or more target volumes while minimizing dose to other tissues. Radiation treatment planning typically involves performing a reverse optimization which starts with a prescribed dose distribution and seeks to optimize parameters for radiotherapy delivery which will most closely approach the prescribed dose. The radiation treatment plan may specify things like:

A type of delivery (e.g. stereotactic body radiation therapy ("SBRT"), intensity-modulated radiation therapy (IMRT), dynamic conformal arc radiation therapy (DCA), volumetric modulated arc therapy (VMAT), image guided radiotherapy (IGRT), Rapidarc™ (RA) etc.

A trajectory such as an arc or set of directions from which radiation beams may be delivered;

Beam shaping to be applied for different directions;

Beam intensity for different directions.

Radiation treatment planning generally takes into account constraints imposed by a linear accelerator or other radiation delivery system to be used. These constraints may arise, for example, from the maximum rates at which different parameters can be changed, achievable physical configurations of the radiation delivery system, available trajectories, the physical construction of a beam shaper etc. In many cases a radiation treatment plan involves optimization to particularly sensitive organs or structures (organs at risk or "OARs").

Optimizing a radiation treatment plan typically involves creating an objective function which defines the goals of the treatment (namely optimizing the planning target volume (PTV) coverage plus a small margin while minimizing dose to nearby normal tissues. A computer system then attempts to optimize the radiation delivery such that the combined objectives are achieved.

In addition to providing a dose distribution that closely matches a desired dose distribution it is desirable to provide a radiation treatment plan that can be delivered in a relatively short period. Linear accelerators ("LINACs") and other radiation sources are expensive pieces of equipment that can be in short supply and shorter treatments are also less unpleasant for patients.

The level of precision actually achieved while delivering a radiation treatment plan depends on the precision of a radiation source as well as the precision with which the position of the target volume is known. Current radiation delivery systems can shape and deliver radiation beams with high precision (e.g. sub-millimeter precision). Some parts of the anatomy can be immobilized for radiation treatment. However in a living subject there are motions that cannot be eliminated (e.g. motions arising from respiration and/or cardiac function that can cause tissues to move).

Ventricular tachycardia (VT) is a rapid, abnormal heart rhythm. VT can lead to sudden cardiac death in patients with heart disease. In such patients, the VT arises predominantly from abnormal myocardial tissue, particularly myocardium that is scarred from a previous injury, such as a myocardial infarction. Within the scar are surviving areas of myocardium that are electrically active and support re-entrant electrical circuits that cause VT. Reentry refers to a loop of abnormal electrical impulse which continues to re-excite the heart at a rapid rate that is incapable of providing a mechanical contraction, leading to a ceased or severely diminished cardiac pumping function.

Current options for treating VT include antiarrhythmic drug therapy and catheter ablation, both of which are associated with issues regarding efficacy and potential complications. Cardiac radiosurgery, external beam therapy targeted at abnormal myocardial tissue, has the potential to be a non-invasive and efficient treatment option for VT. Phillip S. Cuculich et al. *Noninvasive Cardiac Radiation for Ablation of Ventricular Tachycardia* N Engl J Med 2017; 377: 2325-233, Dec. 14, 2017 describes the use of SBRT to treat VT.

There is a need for improved methods and apparatus for planning and delivering radiotherapy.

SUMMARY

In this section, a description of the general features of the present invention or disclosure is given for example by referring to possible embodiments of the invention. Specifically, various aspects of the present disclosure are described in the following. Any feature, element and/or step described in the following with respect to one aspect of the present disclosure equally applies to any other aspect of the present disclosure.

The present invention has a number of aspects. These include, without limitation:
  Methods for radiation treatment planning;
  Methods for radiation treatment delivery;
  Apparatus for radiation treatment planning;
  Apparatus for radiation treatment delivery.

The invention may be applied to treating a range of indications including atrial fibrillation, ventricular fibrillation, ventricular tachycardia, cancer, and other cases where radiotherapy is applicable to treat target volumes in locations which can be affected by motions caused by the cardiac and/or respiratory cycles. For example, the present technology can be applied to spare organs such as the heart, proximal bronchial tree, aorta, and esophagus which move significantly with the cardiac cycle when delivering radiation to treat benign, primary and/or metastatic tumors located on or close to such organs.

It is emphasized that at least some aspects of the invention described herein do not involve or in particular comprise or encompass an invasive step which would represent a substantial physical interference with the body requiring professional medical expertise to be carried out and entailing a substantial health risk even when carried out with the required professional care and expertise. More particularly, certain aspects of the invention do not involve or in particular comprise or encompass any surgical or therapeutic activity. For these reasons alone, no surgical or therapeutic activity and in particular no surgical or therapeutic step is necessitated or implied by carrying out such aspects of the invention.

One aspect provides a method that outputs a set of treatment Arc Segments (AS) defined by a number of parameters (e.g. temporal gantry angle profile, temporal dose rate profile and the temporal multileaf collimator (MLC) leaf motion profiles). Each of these arc segments is delivered during a quiescent interval and collectively the set of arc segments defines the patient's treatment. During treatment, the patient's heart motion is tracked real time for example using a device such as an ECG or other modality for tracking a cardiac cycle.

The acquired data is used to predict the timings and durations of the following quiescent intervals. For the subsequent quiescent interval, the algorithm adjusts the aforementioned machine parameters such that the delivered radiation during the AS is the same as from the initial optimization. This is then repeated until all AS have been delivered.

One example aspect provides apparatus for delivering radiation treatment to a patient. The apparatus comprises a radiation source, a drive connected to move the radiation source along a trajectory relative to the patient, a stored radiation treatment plan specifying a plurality of beam ON segments of the trajectory and specifying a plurality of beam OFF portions of the trajectory interleaved with the plurality of beam ON segments of the trajectory. The apparatus also comprises a monitor connected to detect progress of a physiological cycle of the patient wherein the physiological cycle comprises cycles that include quiescent periods. The apparatus also comprises one or more data processors connected to: control the drive to advance the radiation source along the trajectory; control the radiation source to deliver radiation in each of the plurality of beam ON segments of the trajectory and to deliver no or negligible radiation in each of the a plurality of beam OFF portions of the trajectory; process an output of the monitor to estimate a time for a next one of the quiescent periods; and control a speed at which the radiation source is advanced along the trajectory to cause a next one of the beam ON segments to coincide with the next one of the quiescent periods.

In some embodiments the monitor comprises an electrocardiogram (ECG) and the physiological signal comprises a cardiac signal.

In some embodiments the one or more data processors are configured to: receive an ECG trace from the monitor; process the ECG trace to identify points where a rate of change of the ECG trace exceeds a threshold; within a window around each of the identified points of the ECG trace locate an R peak as a maximum of the ECG trace within the window; and determine a time difference between two most recent adjacent R peaks as a period of the cardiac signal.

In some embodiments determining the estimated time for a next one of the quiescent periods based on the time difference between the two most recent adjacent R peaks.

In some embodiments the monitor comprises one or more of a real time imager coupled with an image processing system a pulse monitor or an impedance based monitor.

In some embodiments the monitor comprises a real time imager coupled to an image processor that includes a model trained to locate metallic cardiac leads in images obtained by the imager and to process locations of metallic cardiac leads determined by the model to determine motions of the metallic cardiac leads.

In some embodiments each of the beam OFF portions of the trajectory is about twice as long as each of the beam ON segments of the trajectory.

In some embodiments the radiation treatment plan comprises a plurality of phases, the one or more data processors are configured to execute the phases in a sequence, each of the phases specifies a plurality of the beam ON segments of the trajectory and a plurality of the beam OFF portions of the trajectory, and the beam ON segments in different ones of the phases are at different locations along the trajectory.

In some embodiments the beam ON segments in the different phases do not overlap with one another.

In some embodiments beam ON segments in the different phases overlap.

In some embodiments a length of the overlap corresponds to a ramp up time for the radiation source.

In some embodiments the plurality of phases comprises three phases and the beam ON segments from all of the three phases collectively cover the entire trajectory.

In some embodiments the apparatus comprises a data store connected to record the output of the monitor and processing the an output of the monitor to estimate a time for a next one of the quiescent periods comprises processing most recent data in the data store.

In some embodiments the one or more data processors are configured to determine a cardiac cycle period from the most recent data in the data store and to estimate the time for a next one of the quiescent periods based in part on the cardiac cycle period.

In some embodiments the one or more data processors are configured to determine a time derivative of cardiac cycle period from the most recent data in the data store and to estimate the time for a next one of the quiescent periods based in part on the time derivative of the cardiac cycle period.

In some embodiments the one or more data processors are configured to advance the radiation source along the trajectory without stopping until at least the end of a last one of the beam ON segments.

In some embodiments the data processors are configured to maintain the speed of the radiation source constant except as required to cause the next one of the beam ON segments to coincide with the next one of the quiescent periods.

In some embodiments the radiation source comprises a linear accelerator.

In some embodiments the radiation source is mounted to a gantry which is rotatable about an axis and the trajectory comprises an arc made by the radiation source as the gantry is rotated between a starting angle and an ending angle.

In some embodiments the one or more data processors are configured to maintain an average acceleration of the gantry to not exceed 0.15 deg/s$^2$ between a start of a first beam ON segment in the trajectory and the end of a last beam ON segment in the trajectory.

In some embodiments the apparatus comprises a variable beam shaper and the radiation treatment plan comprises parameters specifying configurations of the variable beam shaper at least for points along the trajectory in the beam ON segments and the one or more data processors are configured to adjust a speed with which the variable beam shaper is varied among the configurations to match the speed at which the radiation source is advanced along the trajectory.

In some embodiments the beam ON segments have lengths such that each beam ON segment can be delivered in a time not exceeding about 200 ms at a speed that does not exceed a maximum speed at which the drive can advance the radiation source along the trajectory.

In some embodiments the apparatus comprises a radiation treatment planning console providing user controls for specifying a target volume for the radiation treatment plan and generating the radiation treatment plan based at least in part on the specified target volume.

In some embodiments the one or more processors are configured to receive a preliminary radiation treatment plan and to segment the preliminary radiation treatment plan to provide the radiation treatment plan.

In some embodiments the apparatus comprises a user interface providing controls to set one or more of sizes of the segments in the radiation treatment plan and a number of phases to distribute the segments among.

In some embodiments the apparatus comprises a real time imaging system and the one or more data processors are configured to process images obtained from the real time imaging system to locate a metallic lead in the images wherein process an output of the monitor to estimate a time for a next one of the quiescent periods comprises detecting cyclical motion of the metallic lead.

In some embodiments the real time imaging system is a cone beam computed tomography (CBCT) system.

In some embodiments the one or more processors are configured to determine a start time for the next one of the beam ON segments.

One example aspect provides a method for preparing a radiation treatment plan for delivering radiation treatment to a patient. The method comprises generating optimized parameters for delivering a radiation beam from a radiation source moving along a trajectory to irradiate a target volume in a patient and segmenting the optimized parameters into a plurality of phases such that each of the phases specifies a plurality of beam ON segments of the trajectory for which the radiation beam is ON and a plurality of beam OFF portions of the trajectory for which the radiation beam is OFF, wherein the beam ON segments in different ones of the phases are at different locations along the trajectory.

In some embodiments generating optimized parameters comprises receiving a preliminary radiation treatment plan generated by reverse optimization, and segmenting the preliminary radiation treatment plan to provide the beam ON segments and beam OFF portions.

In some embodiments the plurality of phases comprises three phases.

In some embodiments the plurality of phases comprises from two to ten phases.

In some embodiments generating optimized parameters comprises specifying configurations of a variable beam shaper at least for points along the trajectory in the beam ON segments.

In some embodiments the beam ON segments have lengths such that each beam ON segment can be delivered in a time not exceeding about 200 ms by a radiation delivery system associated with the plan In some embodiments the plurality of phases comprises three phases and the beam ON segments from all of the three phases collectively cover the entire trajectory.

Another example aspect provides a method for preparing a radiation treatment plan for delivering radiation treatment to a patient. The method comprises generating optimized parameters for delivering a radiation beam from a radiation source moving along a trajectory to irradiate a target volume in a patient subject to the constraint that the radiation beam is ON only for beam ON segments of the trajectory and is OFF in beam OFF portions of the trajectory between adjacent ones of the beam ON segments.

In some embodiments each of the beam OFF portions is approximately twice as long as the beam ON segments.

In some embodiments the method comprises segmenting the optimized parameters into a plurality of phases such that each of the phases specifies a plurality of beam ON segments of the trajectory for which the radiation beam is ON and a plurality of beam OFF portions of the trajectory for which the radiation beam is OFF, wherein the beam ON portions in different ones of the phases are at different locations along the trajectory.

In some embodiments the beam ON segments in the different phases do not overlap with one another.

In some embodiments the radiation source has a ramp-up time and a ramp-down time during each beam ON segment, and beam ON segments in the different phases overlap so that for each beam ON segment a ramp-up time of that beam ON segment coincides with a ramp-down time of a different beam ON segment.

In some embodiments the plurality of phases comprises three phases and the beam ON segments from all of the three phases collectively cover the entire trajectory.

In some embodiments the beam ON segments have lengths such that each beam ON segment can be delivered in a time not exceeding about 200 ms by a radiation treatment system specified by the radiation treatment plan.

In some embodiments generating optimized parameters comprises receiving a preliminary radiation treatment plan, and segmenting the preliminary radiation treatment plan to provide beam ON segments and beam OFF portions.

A further example aspect provides a method for controlling a position of a radiation source of a radiation delivery system along a trajectory. The method comprises reading a radiation treatment plan specifying locations along the trajectory of a plurality of beam ON segments and a plurality of beam OFF portions interleaved between the beam ON segments, processing an output of a patient monitor to estimate a starting time for starting a next one of the beam ON segments such that the beam ON segment will coincide with a quiescent period, and adjusting a speed at which the radiation source is being driven along the trajectory to cause the radiation source to arrive at the location along the trajectory corresponding to the next one of the beam ON segments at the starting time.

In some embodiments the output of the patient monitor comprises an electrocardiogram (ECG) trace and the method comprises processing the ECG trace to identify points where a rate of change of the ECG trace exceeds a threshold, locating within a window around each of the identified points of the ECG trace an R peak as a maximum of the ECG trace within the window, determining a time difference between two most recent adjacent R peaks as a period of a cardiac signal, and designating a duration that is a first fraction of the period of the cardiac signal and starting a second fraction after each R peak as a quiescent period.

In some embodiments the first fraction and the second fraction are each about one third.

In some embodiments the method comprises determining a specified configuration for a variable beam shaper specified by the radiation treatment plan for the start of the next beam ON segment and driving elements of the variable beam shaper at constant speeds selected to cause the variable beam shaper to have the specified configuration at the starting time.

In some embodiments the method comprises updating the starting time and adjusting the speed at which the radiation source is advanced along the trajectory according to the updated starting time.

It is emphasized that features, functions, elements and/or steps, which are described above and in the following with reference to one aspect of the invention or disclosure, equally apply to any other aspect of the invention or disclosure described above and in the following. Particularly, features and/or elements, as described above and in the following with reference to the apparatus according to the first aspect, equally apply to the method according to the second aspect, and/or the apparatus according to the third aspect, and vice versa.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

FIG. 1B shows the example case where an original radiation treatment plan is segmented into three phases.

FIG. 4 is a sketch that illustrates features of a typical ECG signal.

FIG. 7A shows dose isolines and FIG. 7B shows dose profile comparing an original VMAT treatment plan and a CSVMAT plan.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

One aspect of the present technology exploits the facts that at least some motions that can interfere with the accuracy of radiation treatment are cyclical and that the cycles of the motions include quiescent intervals. Delivery of radiation by a dynamic radiation delivery protocol is controlled such that the radiation is delivered in the quiescent intervals and not in other periods. For example, radiation beam delivery for radiation treatment may be synchronized with a cardiac signal, irradiating only during the quiescent intervals of the cardiac cycle (when heart motion is minimal) and adjusting the beam delivery speed in response to any changes in heart rate. When applied to ameliorate the effects of motions resulting from the cardiac cycle embodiments of the present technology that deliver radiation by a VMAT protocol may be called cardiac synchronized volumetric modulated arc therapy (CSVMAT).

Figure 1:
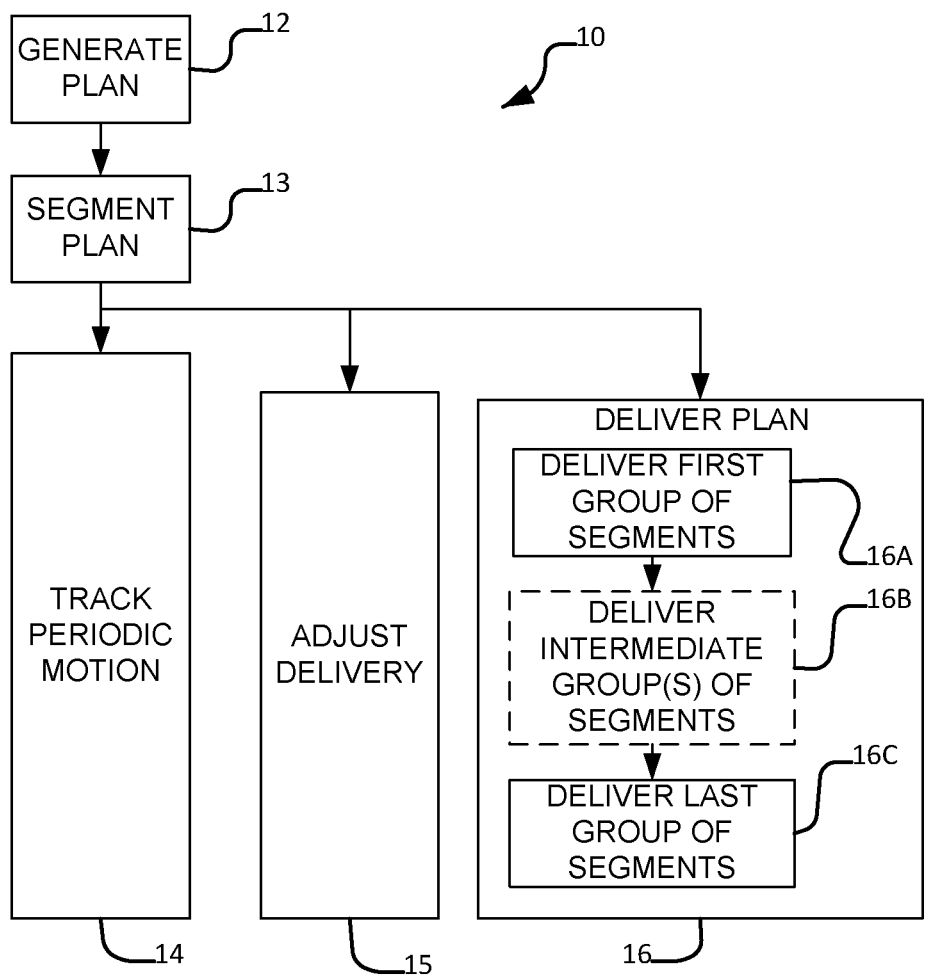
FIG. 1 is a flow chart illustrating an example embodiment of the invention.

FIG. 1 is a flow chart that illustrates a method 10 according to a simple embodiment of the present technology. At block 12, method 10 generates an optimized radiation treatment plan for delivering prescribed radiation dose to a target volume or target volumes. The plan is a dynamic plan. Here, "dynamic" means that the plan specifies that radiation is delivered while parameters of a radiation delivery system are being changed. A dynamic plan is in contrast to a "point and shoot" plan in which parameters remain fixed while radiation is delivered.

An example of a dynamic plan is a plan that specifies that radiation is to be delivered while a radiation source is moving relative to a patient along a trajectory such as an arc. The plan may specify how other parameters of a radiation delivery system such as beam shaping parameters (e.g. multileaf collimator leaf positions and/or collimator rotation angles), beam parameters (e.g. monitor units ("MU")) etc. are to be changed with the position of the radiation source along the trajectory.

In some embodiments the plan specifies values for parameters at control points spaced apart along the trajectory. For points on the trajectory between the control points the parameters may be set by interpolation between the closest control points.

Block 12 may be performed using commercially available radiation treatment planning software.

In block 13 the plan is divided into segments that can each be delivered in a quiescent interval of the motion or motions of concern. For example, where motion arising from the cardiac cycle is of concern the segments may each be deliverable within a quiescent interval within one cardiac cycle.

The segments are arranged in interleaved groups. For example if each segment is identified by an index i with i ε [1, 2, 3 . . . ] then a first group may include all of those segments for which i=1+ng where g is the number of groups and n is any whole number [0, 1, 2, 3 . . . ], a second group may include all of those segments for which i=2+ng and so on. Usually 2 or 3 groups are sufficient.

Where motion arising from the respiratory cycle is of concern the groups may each comprise a series of the segments wherein the entire series of segments is of such a length that the segments of the group are all deliverable within one quiescent interval of the respiratory cycle or the groups may be divided into sub-groups where each of the sub-groups includes a series of the segments wherein the series of segments is of such a length that the segments of the sub-group are all deliverable within one quiescent interval of the respiratory cycle. In some embodiments a plurality of the sub-groups spans the trajectory.

Figure 1A:
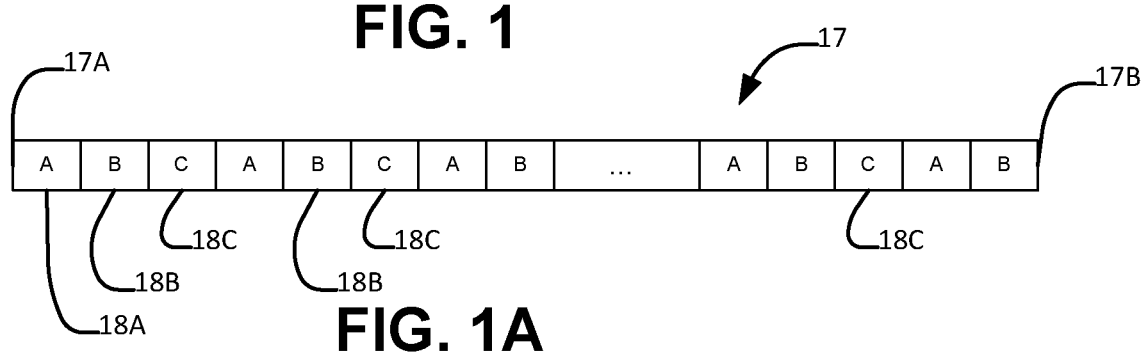
FIG. 1A is a schematic illustration of a radiation treatment plan that has been segmented.

FIG. 1A shows an example trajectory 17 divided into segments 18A, 18B, 18C (collectively or generally segments 18) belonging to three groups A, B and C. It is not mandatory that there be the same number of segments in each group. Trajectory 17 starts at an initial position 17A (e.g. an initial gantry angle) and ends at final position 17B (e.g. a final gantry angle).

In some embodiments the segments in the different groups do not overlap with one another. For example, one segment may span a portion of an arc from angle A+ to angle B−. A next segment may span an adjoining portion of the arc from angle B+ to angle C− and so on.

Figure 1B:
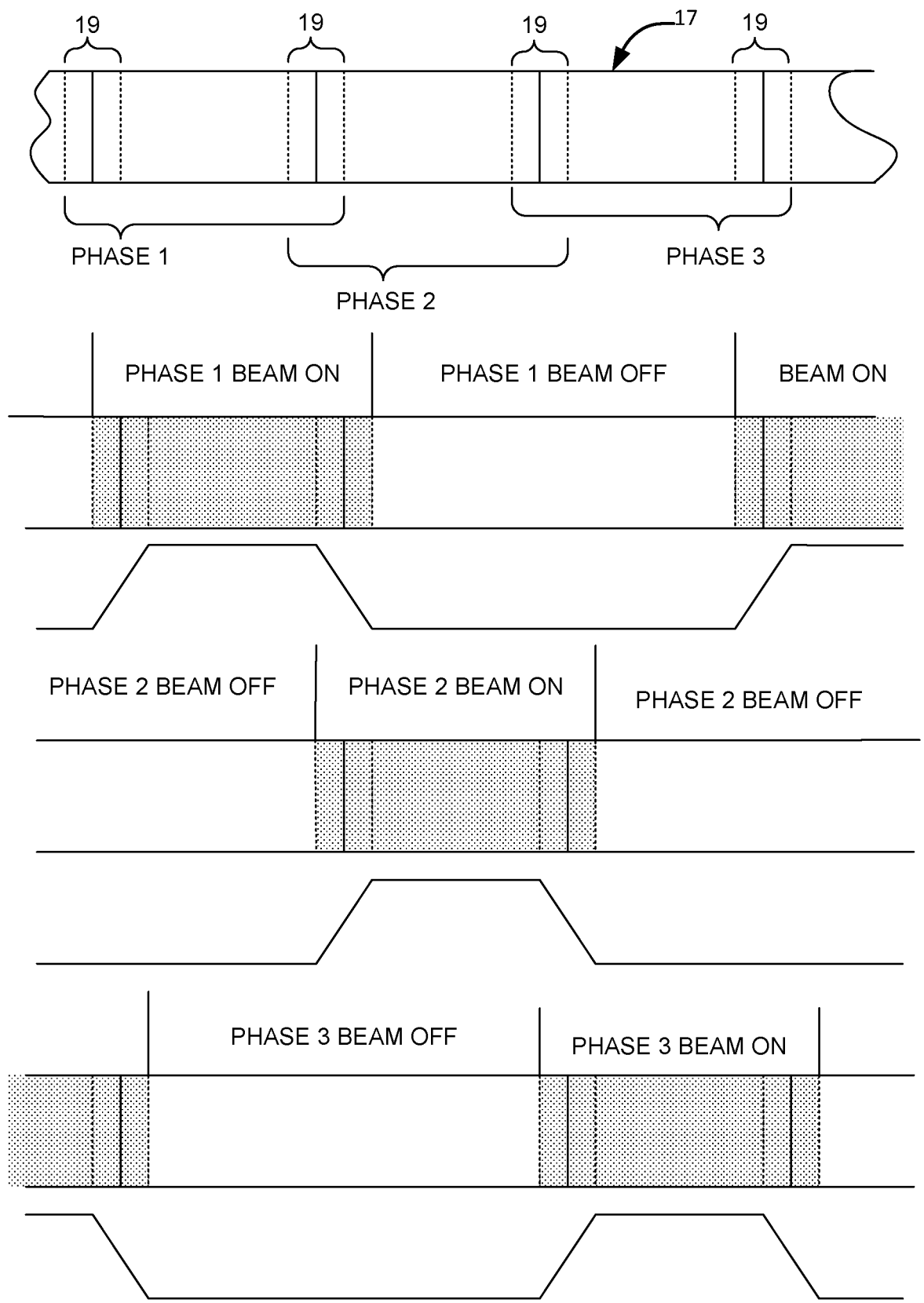
FIG. 1B is a timing diagram that illustrates an alternative way to segment a radiation treatment plan that takes into account the time taken for a radiation beam to ramp up or down in intensity.

In some embodiments segments that are adjacent to one another along a trajectory may overlap. For example, where a radiation delivery system is used that requires some time for beam intensity to ramp up to a set value or to ramp down from the set value then the ramp down of one segment may overlap with the ramp up of a next segment along the trajectory. This is illustrated in FIG. 1B in which original radiation treatment plan 17 is segmented into three phases. FIG. 1B schematically illustrates radiation beam intensity below each phase. Portions 19 of the original radiation treatment plan 17 which correspond to times required for a radiation beam to be ramped up to or down from a set intensity are present in two phases.

In block 14 the periodic motion is tracked. Block 14 may, for example comprise one or more of:
- tracking an ECG signal and/or
- tracking a pulse signal (e.g. by a pulse oximeter or other known pulse detection technology) and/or
- using a magnetic resonance imaging (MRI) navigator to track a cardiac cycle and/or
- using a sequence of images (e.g. fluoroscopy or planar kV images) to measure tissue motions; and/or
- tracking bioimpedance measurements.

Based on the tracking, the timing of quiescent intervals is determined.

In block 16 the radiation specified by the radiation treatment plan is delivered. The delivery is performed in as many dynamic passes through the trajectory (phases) as there are groups of segments. For example, block 16A controls a radiation delivery system to pass once through a specified trajectory delivering radiation only for segments 18 in a first group of segments (e.g. group A), block 16B controls the radiation delivery system to pass once through the specified trajectory delivering radiation only for segments 18 in one or more intermediate groups (e.g. Group B) and block 16C controls the radiation delivery system to pass once through the specified trajectory delivering radiation only for segments 18 in a final group (e.g. Group C). The radiation delivery system may be controlled to inhibit delivery of radiation in parts of the trajectory that are not in the segments being delivered. The radiation delivery system may move the radiation source continuously in each of blocks 16A, 16B and 16C.

While block 16 is being performed, block 15 adjusts delivery so that the radiation delivery system will pass through each of the segments for which radiation is being delivered in the current pass though the trajectory during a corresponding quiescent interval. Block 15 may, for example, speed up or slow down motion of the radiation delivery system so that the radiation source will arrive at a position that corresponds to the start of the next segment in the group for which radiation is being delivered in the current pass through the trajectory at or only slightly after the start of a quiescent interval such that the radiation for the segment can be completely delivered within the quiescent interval. Preferably in each of blocks 16A, 16B and 16C, one segment is delivered for each period of a cycle (e.g. a cardiac cycle).

Figure 2:
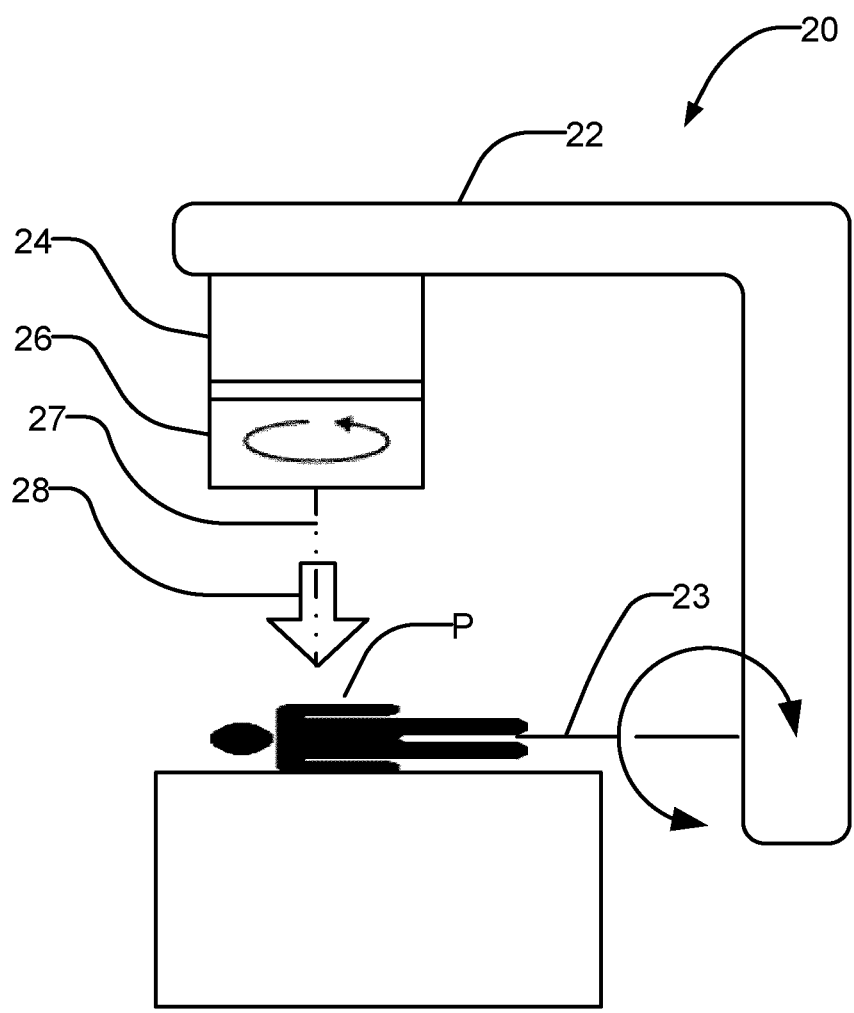
FIG. 2 is a schematic illustration of an example radiation delivery system.

FIG. 2 is a schematic illustration of an example radiation delivery system 20. System 20 includes a gantry 22 that supports a radiation source 24. Gantry 22 is rotatable about axis 23 to move radiation source 24 in an arc around a patient P. A beam shaper 26 such as a multileaf collimator is provided to shape a radiation beam 28 emitted by radiation delivery system 20. Beam shaper 26 is rotatable about an axis 27.

A more detailed example embodiment will now be described. As mentioned above, generating an optimized radiation treatment plan may be performed using commercially available radiation treatment planning software. Such software is available from companies such as Varian, Elekta, Phillips and Brainlab. A radiation treatment plan typically comprises a set of instructions that define a trajectory and, for control points along the trajectory, specify values for parameters such as radiation output (e.g. in monitor units), beam shaper configuration, beam shaper rotation angle etc. The instructions of the radiation treatment plan may be provided to a radiation delivery system. The radiation delivery system can then execute the instructions to deliver radiation according to the radiation treatment plan.

Segmenting a radiation treatment plan may be done without any modification to the process of radiation treatment planning. However, as described below, radiation treatment planning may be modified to facilitate providing a segmented radiation treatment plan.

A radiation treatment plan may be segmented in ways including:

Running the radiation treatment plan on a radiation delivery system 20 while logging the configuration of the radiation delivery system. The resulting log provides a set of actual parameter values measured by the radiation treatment system for small increments of travel along the trajectory specified by the radiation treatment plan. For example, the log maintained by the Varian TrueBeam linear accelerator used for proof of concept studies for the present technology records the parameter values (including machine component positions) every 20 ms. The log data is essentially a modified version of the radiation treatment plan in which every increment of travel is a control point. The log data additionally includes time information indicating when the radiation treatment system reached each point along the specified trajectory. This modified radiation treatment plan can then be divided into interleaved segments.

Running the radiation treatment plan on a software based simulator that accurately mirrors the performance of a particular radiation treatment system 20. The simulator may take into account factors such as acceleration rates and rates of change for the parameters that result when the radiation treatment system executes a radiation treatment plan which changes values of the parameters. An output of the simulation may be a set of log data that the simulator predicts would be generated if the radiation treatment plan were run on the radiation delivery system 20.

Generating the segmented radiation treatment plan using radiation treatment planning software that has been modified to output a segmented radiation treatment plan. The segmented treatment plan may, for example comprise plural interleaved phases as discussed herein or a single phase having separated beam ON segments which has been optimized to provide the prescribed radiation dose. Where the segmented radiation treatment plan includes plural phases it is not mandatory that all of the phases be delivered from the same trajectory (e.g. the same arc). Different ones of the phases may be delivered from different trajectories (e.g. different arcs) thereby providing further opportunity for optimization. Optimization may take into account radiation delivery system limitations such as the time derivative of the dose rate in ramps (e.g. 47A, 47B) between beam ON and OFF states to further improve plan fidelity.

In some embodiments treatment planning optimization includes selecting a maximum intensity for the radiation beam. By increasing the intensity to which the radiation beam is ramped in the beam ON segments the dose delivered in each beam ON segment may be increased, thereby reducing the time needed to deliver a prescribed dose. On the other hand, increasing beam intensity without increasing the speed of travel of the radiation source can cause increased dose to be delivered to some tissues outside of the target volume. If the radiation delivery system is capable of high enough beam intensity, the upper limit of beam intensity is achieved when the beam must immediately start ramping down in intensity to be at zero or negligible intensity by the end of the current beam ON segment.

A plan (or log) may be segmented by dividing it into segments in which each individual segment can be delivered within one quiescent interval of the motion in question. Where the motion results from the cardiac cycle can be convenient to group the segments into three interleaved phases because often the quiescent interval in the cardiac cycle occupies a bit more than one third of the period of the cardiac cycle. Each of the phases may be delivered in a separate traversal of the trajectory. The combination of the interleaved beam deliveries recreates the original plan. In some embodiments there are in the range of one to ten phases.

In an example case the trajectory is an arc and each of the segments is associated with a corresponding segment of the arc ("AS").

For example, approximately the first 200 ms segment of the plan may be assigned to the first phase. The second and third approximately 200 ms segments may be assigned to the second and third phases respectively. The remaining segments may be assigned among the phases in a round robin manner. The result is that each phase specifies a repeating pattern of about 200 ms beam ON and about 400 ms beam OFF.

An interval of about 200 ms is a good choice for the duration of each segment because 200 ms easily fits within the quiescent interval of the cardiac cycle over a broad range of heart rates (up to 100 beats per minute)—the beam delivery speed can be decreased as necessary for lower heart rates.

Figure 3:
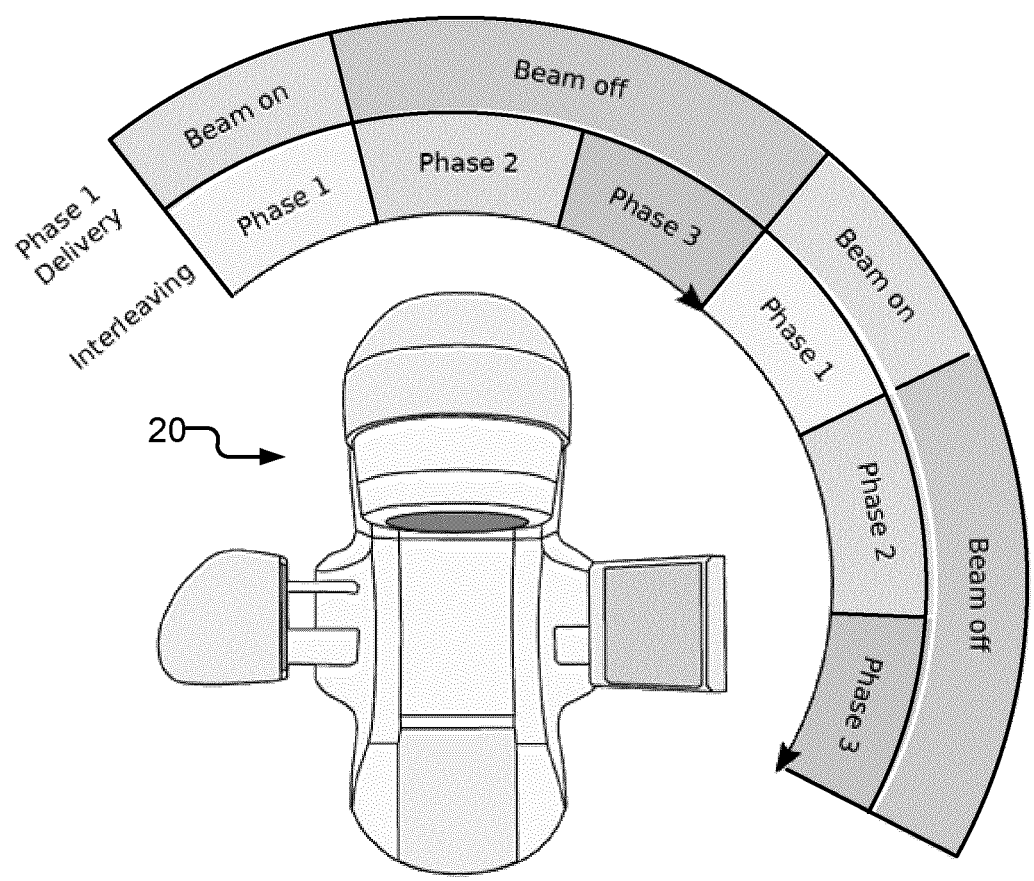
FIG. 3 illustrates segmenting a radiation treatment plan and allocating segments to different phases.

FIG. 3 conceptually illustrates the allocation of different segments of a plan among three phases. For ease of illustration the sizes of the segments are exaggerated in FIG. 3.

By breaking a radiation treatment plan into interleaved phases the phases can be applied in sequence to control the radiation delivery system (e.g. linear accelerator) to turn the beam ON at specific times while traversing a trajectory (e.g. by rotating the linear accelerator gantry head). Importantly it is not necessary to stop the gantry every time the beam turns OFF. The gantry head may be moving continuously throughout the delivery of each phase of the radiation treatment plan. Large accelerations of the speed at which the trajectory is traversed can advantageously be avoided.

In delivering each phase the source of motion (e.g. cardiac cycle) is monitored and the delivery of the phase is adjusted in real time to maintain synchronization between the segments within the phase during which radiation is delivered and the quiescent intervals of the motion. Interleaving using 3 phases in which the beam is turned on in diastole of every heartbeat allows delivery of a radiation treatment plan with smooth gantry motion while avoiding delivering radiation during movements caused by the cardiac cycle.

In some embodiments the direction in which the trajectory is traversed alternates as each phase is delivered. For example, a trajectory may comprise an arc extending from a first gantry angle to a second gantry angle. A first phase may be delivered while a gantry of a radiation delivery system is moved along the trajectory from the first angle to the second angle. A second phase may be delivered while the gantry is moved from the second angle back to the first angle. A third phase may be delivered while the gantry is moved from the first angle to the second angle. This may allow a segmented radiation treatment plan having plural phases to be delivered in a shorter time then might be required if all of the phases were delivered with the radiation source traversing the trajectory in the same direction.

The cardiac cycle is periodic, with the time between subsequent heart beats being very consistent over short periods of time. However, the heart rate is variable. Even small changes in heart rate can result in de-synchronization between the planned treatment and the quiescent cardiac intervals. De-synchronization can result in delivery of radiation during high-motion parts of the cardiac cycle, which should be avoided. To maintain synchronization delivery, parameters are actively adjusted during treatment in response to a patient's change in heart rate. For example, the heart rate may be tracked in real time using an ECG and the acquired heart rate data may be used to predict timings and durations of following quiescent intervals.

The adjustment can include one or more of:

For each quiescent interval adjusting the dose rate, multi-leaf collimator speed, and gantry speed so that the beam-on segment duration fits within the quiescent interval.

Between quiescent intervals, adjusting the speed at which the trajectory is traversed (e.g. gantry speed) so that the beam source will be positioned at the location on the trajectory (e.g. gantry angle) corresponding to the next "beam ON" segment for the current phase early enough in a quiescent interval for delivery of the segment to be completed before the end of the quiescent interval.

The adjustment may be carried out in a way that acceleration of the motion of the radiation source is gradual. This is facilitated by the fact that during beam OFF periods it is not important exactly where the radiation source is.

Within each beam ON segment in each phase, beam shaping parameters (e.g. MLC leaf positions and MLC rotation angle) for each point along the trajectory (e.g. gantry angle) can be identical to the original plan. During beam-off segments the beam shaping parameters may vary along the trajectory as specified the original plan. However, there is no need for beam shaping parameters to follow the original trajectory. In beam OFF periods within each phase, each machine axis (e.g. leaf position, beam shaper rotation angle etc.) may be controlled to move in any convenient way toward the initial position for that machine axis in the next beam-on segment of the current phase. For example, each axis may be moved linearly (at a constant speed) with the speed determined according to the length of time ($T_{beam-off}$) between the end of the last beam ON segment and the start of the next beam ON segment. This is illustrated in FIG. 3A.

Figure 3A:
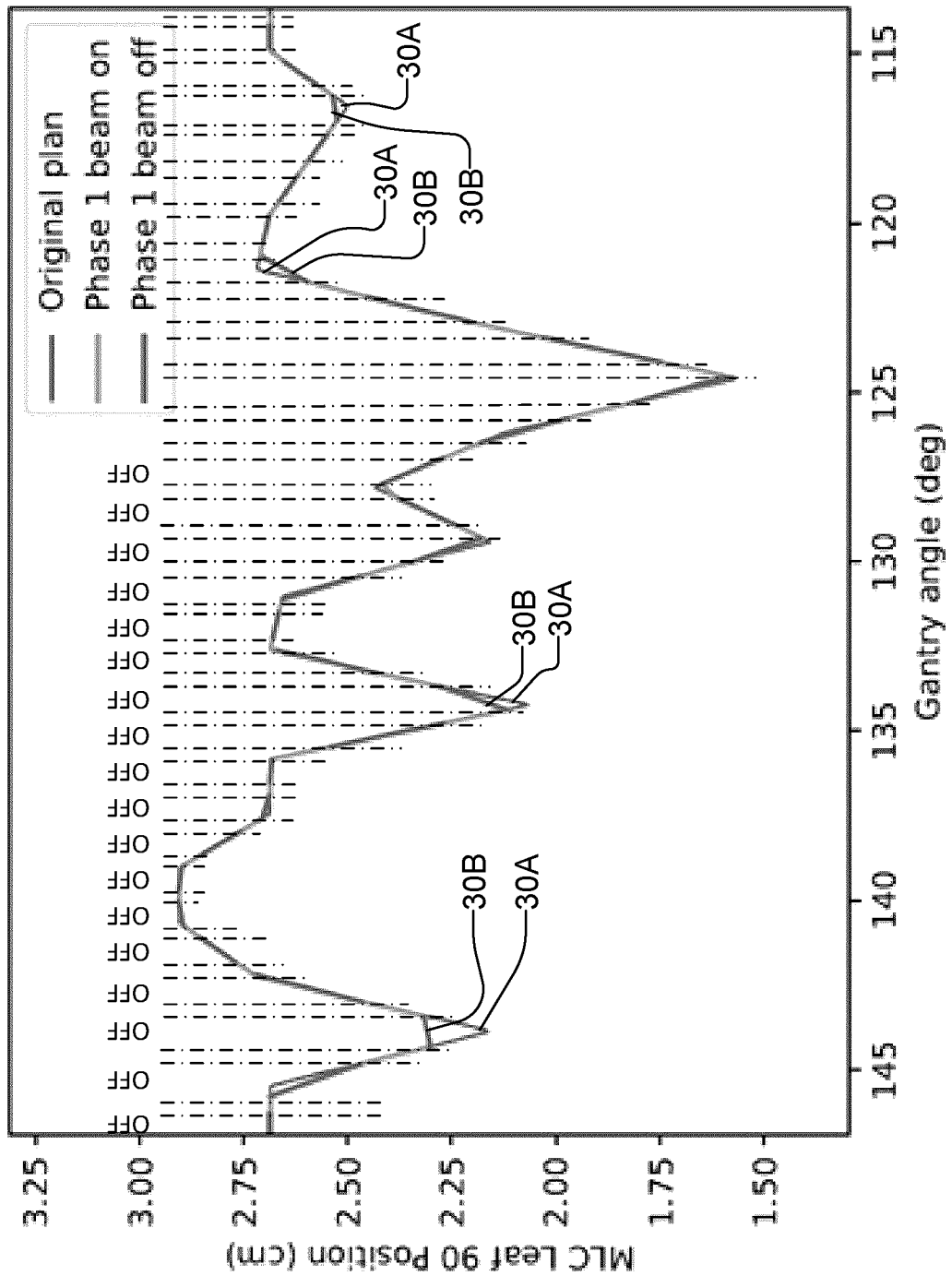
FIG. 3A provides a comparison of a trajectory of a machine component for an original radiation treatment plan and one phase of a segmented radiation treatment plan.

FIG. 3A shows the variation in position for a MLC leaf in an example treatment plan. The vertical dashed lines indicate boundaries between beam ON segments and beam OFF periods. 30A indicates positions specified by an original radiation treatment plan. 30B indicates positions for the MLC leaf in one phase of a segmented plan. It can be seen that 30A and 30B can diverge significantly during beam OFF periods. Effectively, as illustrated by line 30B, positions of a machine axis can be moved during beam OFF periods in a short cut to the position for that machine axis at the start of the next beam ON segment.

Figure 4A:
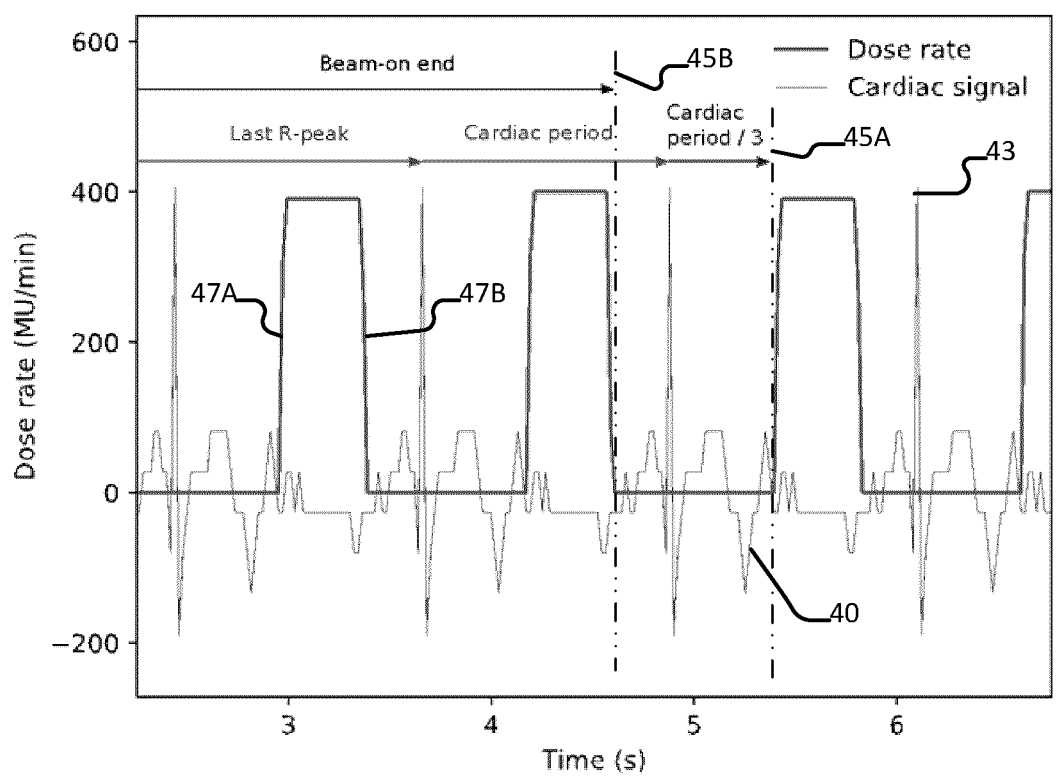
FIG. 4A illustrates synchronization of segments of a radiation treatment plan to a cardiac cycle.
Figure 4B:
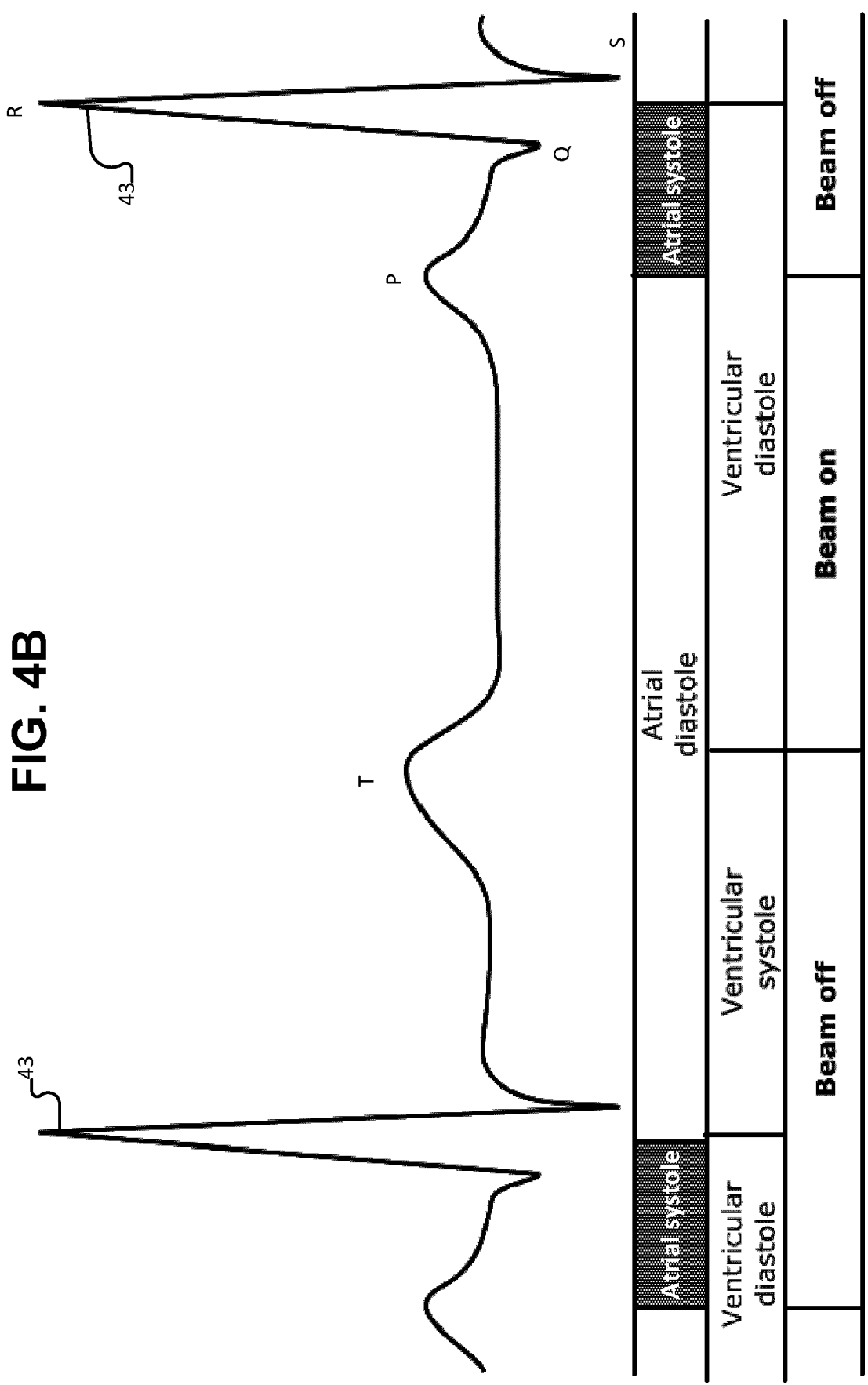
FIG. 4B shows how beam ON and beam OFF periods can be aligned with one period of an ECG signal.

FIG. 4 shows an electrocardiogram ("ECG") trace 40 of an example cardiac cycle. Trace 40 includes peaks commonly identified as P, Q, R, S and T. Trace 40 is periodic. Each period includes a QRS complex 42. The R peak 43 in QRS complex 42 is very distinctive and makes a good timing reference signal although other features of trace 40 may be monitored in addition or in the alternative to R peak 43.

The period T1 of one cardiac cycle is variable. In adult humans the heart typically beats in the range of 40 to 120 beats per minute with 60 to 100 beats per minute typical. T1 is therefore usually in the range of 500 ms to 1500 ms with 600 ms to 1000 ms being typical. The heart rate of any individual is not constant but can vary significantly.

Each cardiac cycle includes a portion called systole during which the heart contracts to expel blood and a portion called diastole during which the heart relaxes and is refilled with blood. Heart motion is greatest during the systolic (contraction) phase of the cardiac cycle.

Schechter et al. determined that areas of the right coronary artery (RCA) can move up to 30 mm during the contraction phase, while the left coronary tree had a displacement of 16.2 mm due to cardiac motion. Hofman et al. determined from cross-sectional MR images maximum in-plane displacements of 25±5 mm for the RCA and greater than 9 mm for the left coronary arteries. Saranathan et al. reported peak RCA displacements of about 15 to 20 mm using magnetic resonance (MR) imaging.

The diastole usually commences at or after the peak of the T wave part of ECG signal 10. Diastole has a number of phases. Heart motion is the least in the diastasis phase 44 which occurs in the middle of diastole after the initial passive filling of the heart's ventricles has slowed down and before the atria contract to complete active filling.

In general for heart rates up to 100 beats per minute the heart is quiescent for a period of at least about 200 ms in each cardiac cycle. The onset of the quiescent interval has a known relationship to features in ECG trace 40. For example, a time that is one third of a cardiac cycle later than an ECG R peak 43 is generally close to the beginning of a quiescent interval that may be exploited as described herein.

In an example embodiment an ECG waveform is processed to detect R-peaks. This can be done by looking for a change in signal amplitude that exceeds a threshold value. The maximum signal value within a defined time window around the detected change in signal amplitude may be identified as an R-peak 43.

The period (T1) of the cardiac cycle may be monitored by measuring the time between R-peaks. The period of the most recent complete cardiac cycle ("current period") or a combination of the most recent cardiac data may be used to predict the start of a next quiescent interval in which radiation will be delivered. For example, the beam may be turned ON one third of the cardiac period after each R peak. This is illustrated by line 45A in FIG. 4A. As another example, a prediction algorithm may take into account the periods of a set of two, three or more of the most recent cardiac cycles and the location of the quiescent period in the set of cardiac cycles to determine a time at which the radiation source should be in position for the start of the next beam ON segment. The prediction algorithm may, for example determine:

a rate of change of the period, a rate of change of the time between the start of a period (e.g. an R peak) and the beginning of the quiescent interval, a rate of change of the time between the start of a period (e.g. an R peak) and the end of the quiescent interval and/or a rate of change of a length of the quiescent interval.

The algorithm may base the time determined for the start of the next beam ON segment on one or more of these factors such that the beam ON segment can be delivered entirely within the next quiescent period. The timing of the start and/or end of the quiescent period in previous cycles may be determined, for example, by real time imaging, Doppler ultrasound, or other sensing of cardiac induced motions.

The beam may be kept ON for a duration equal to a fraction (e.g. one third) of the current period that is expected to correspond to and fall within a quiescent interval. Since the cardiac period may have changed since the "current period" was measured, a beam-ON interval may begin earlier or later than the ideal time. To ensure synchronization is maintained with a changing heart rate, the time to the next beam ON can be calculated from the most recent cardiac (e.g. ECG) data.

During treatment the patient's heart rate may be monitored. If it is not possible to maintain synchronization of the radiation delivery system and the patient's cardiac cycle, (e.g. due to linear accelerator machine limitations) then treatment may be paused. In some embodiments a decision to pause treatment is based on a measure of a reduction in the fidelity with which delivery of the radiation treatment plan will achieve the prescribed dose. For example, if real time monitoring of motion of the heart and/or target volume is available the decision to pause treatment may be automatic and based on a measure of aggregate motion during a most recent beam ON segment. In some embodiments a decision to pause treatment is based on an acceleration that would need to be applied to the motion of the radiation source along the trajectory to reach the starting point for the next beam ON segment exceeding a threshold acceleration.

If treatment is paused, the treatment may be resumed when the patient's heart rate reaches a value closer to that used in optimization. At this point treatment can continue as before.

There is significant room for adjustment of a segmented radiation treatment plan so that individual segments can be delivered in quiescent periods of the patient's cardiac cycle. These include:

varying the speed at which the radiation source is moved along the trajectory (and simultaneously increasing the intensity of the radiation beam). Moving the radiation source faster reduces the time needed to deliver a segment. However if the radiation source is moving along the trajectory too fast after the segment has been delivered then the radiation source may reach a point on the trajectory corresponding to the next beam ON segment before the next quiescent period. In such cases, to maintain synchronization it may be necessary to brake motion of the radiation source and to then accelerate in time to deliver the next beam ON segment. However, it is generally desirable to move the radiation source smoothly through its trajectory without too much acceleration.

varying the size of each segment . Making a segment smaller (e.g. covering a smaller part of the trajectory) allows delivery of the segment in a shorter period of time. However, if the segments are made shorter delivering an entire radiation treatment plan may require more passes through the trajectory, which may increase the time required to deliver radiation as specified by the radiation treatment plan.

increasing or decreasing the portion of the cardiac cycle that is deemed to be a quiescent period. For some applications where atrial systole is found to have an acceptably minor impact on the target motion, beam ON segments may be extended into the atrial systole, thereby allowing delivery of more of a radiation treatment plan within a single (extended) quiescent period.

The above parameters may be adjusted to prepare a segmented radiation treatment plan that is readily synchronized with a patient's cardiac cycle. These parameters are interrelated.

The length of time required for a radiation beam to deliver a desired dose of radiation depends on the intensity of the radiation beam that a radiation source emits. In theory, a radiation treatment plan could be delivered in half of the time if the intensity of the radiation source is doubled. However, where the radiation treatment plan is a dynamic plan delivered when the radiation treatment source is moving along an arc or other trajectory the degree to which delivery of the dynamic radiation treatment plan can be sped up is limited by the maximum speed at which the radiation source can be driven to move along the trajectory.

The degree to which segments of a radiation treatment plan can be made shorter can also depend on limitations of a radiation source. For example, most linear accelerators do not increase or decrease beam intensity instantaneously. Instead beam intensity ramps up or down at a rate which depends on the characteristics of the linear accelerator (see e.g. ramp up 47A and ramp down 47B in FIG. 4A). For example, a linear accelerator that was used to demonstrate proof of principle of the present technology required approximately 40 ms to ramp from zero to 800 MU/min, If individual segments are made too short then it may not be possible for the beam intensity to ramp up enough and subsequently ramp down all within the time available to deliver the segment and still deliver a sufficient dose of radiation.

In one embodiment a VMAT plan is segmented into 3 interleaved arc segment (AS) plans, where each individual AS is deliverable in the quiescent cardiac interval. In one embodiment, an alternating 200 ms beam ON and 400 ms beam OFF pattern is deployed for each phase. The interleaving pattern controls the linear accelerator to turn the beam ON at specific times while rotating the linear accelerator gantry head, without having to stop the gantry every time the beam turns OFF. Alternative time intervals compatible with the operating envelope of the linear accelerator that continue to enable the patient heart or other tissue to be treated in quiescent intervals may be utilized for individual patients and their associated heart rates.

Timing of the cardiac cycle may be monitored in other ways in addition to or as an alternative to monitoring an ECG waveform. For example, timing of the cardiac cycle may be monitored by measuring a patient's pulse or by detecting motions of fiducial markers using a suitable imaging modality.

The methods and apparatus as described herein may be applied in any context where it is desired to deliver radiation to tissues that are affected by periodic motions (e.g. motions arising from the cardiac and/or respiratory cycles). For example the methods may be used to deliver radiation to the heart (e.g. for treatment of VT) or to other tissues e.g. to treat cancer in tissue and organ sites susceptible to respiratory motion including but not limited to lung and liver.

Consider the example case in which it is desired to deliver radiation to a target volume that is in the heart (e.g. to treat VT for example by cardiac stereotactic ablative radiotherapy also known as stereotactic arrhythmia radioablation (STAR)). The techniques as described above may be applied to take cardiac motion into consideration to improve treatment fidelity and minimize the radiation dose outside the target volume. The present technology can reduce dose to healthy cardiac and other surrounding tissues by irradiating only during diastole (quiescent intervals), when heart motion is minimal. Treatment delivery speed may be dynamically varied in response to changes in the intrinsic heart rate. The present techniques may allow treatment planning using a smaller planning target volume (PTV) thereby providing an opportunity to reduce radiation dose to normal areas surrounding the arrhythmogenic target region.

The methods and apparatus as described herein can provide various advantages over standard gating techniques as are used for respiratory motion. Standard gating techniques generally have to recover portions of the treatment arc that are missed as the linear accelerator slows down after treatment stops when the target passes outside the gating window (the linear accelerator cannot stop instantaneously when the beam turns off). When the present technology is applied, the beam OFF times can be inherently incorporated into the treatment and thus no portions of the arc need to be recovered due to gantry overshoot. This can allow radiation treatment plans to be delivered more quickly using the methods described herein than they could be delivered using standard gating techniques in which gantry motion is stopped each time a gating window is exited. Additionally, by minimizing mechanical accelerations of both the MLC and the gantry, the present techniques may contribute significantly less mechanical stress to the linear accelerator, likely reducing the required maintenance and/or increasing linear accelerator longevity.

The techniques described herein can beneficially be applied to deliver radiation using conventional linear accelerators that are widely available due to their use in cancer treatment. VMAT treatments, however, are negatively impacted by target motion.

In some embodiments the methods and apparatus described herein are applied to reduce or eliminate the effect of motions arising from the cardiac cycle and are combined with other techniques such as deep inspiration breath hold (DIBH), abdominal compression, respiratory gating, respiratory cycle tracking and/or active breathing control, to address movement arising from breathing.

Some embodiments time delivery of radiation to quiescent intervals of two different cycles. For example, the present technology may be applied to synchronize delivery of radiation to quiescent intervals in both a cardiac cycle and a breathing cycle. In such embodiments, patient breathing and heart rate data may be acquired simultaneously, for example using a respiratory and cardiac monitoring system as described in Kohli, K. et al. *Prototype development of an electrical impedance based simultaneous respiratory and cardiac monitoring system for gated radiotherapy. Biomed. Eng. OnLine* 13, 144 (2014). The comparatively long period of the respiratory cycle makes breathing motion simpler to address than motion causes by the cardiac cycle.

In some cases, cardiac pacemaker programming or asynchronous mode may be provided to help regulate cardiac rhythms to facilitate use of the techniques described herein.

For treatment sites susceptible to respiratory motion (such as lung or liver) the methods described herein may beneficially reduce radiation dose to normal tissues due to the reduced need to account for motion uncertainty by increasing the treatment volume(s). Larger treatment volumes are generally associated with higher peripheral dose.

Where it is desired to compensate for respiratory motion it is beneficial to have an accurate tool for directly detecting the respiratory motion. One way to directly monitor respiratory motion is to track the position of a target that is caused to move by the respiratory motion. In some embodiments, respiratory motion and/or cardiac motions are tracked by monitoring the position of a device that is implanted in the heart. This is particularly valuable when the target volume is in the heart because the motion of the implanted device is then a good surrogate for the motion of the target volume. Conveniently, many patients eligible for STAR have implanted cardiac defibrillators (ICDs) which include leads that are located in the heart. Using ICD leads as internal fiducials for motion tracking is advantageous because: the locations in which ICD leads are placed makes them suitable as motion surrogates for targets within the heart, ICD leads are easily identifiable in kV images, and in many cases ICD leads are already present so that additional invasive surgery to implant fiducial markers is not necessary.

One way to identify and track the motions of ICD leads in the heart is to train a deep neural network to recognize such leads in image data. The detection model may be trained on a dataset consisting of kV images of cardiac leads positioned in various orientations.

Experiments have shown that it is feasible to perform real time cardiac lead detection using standard cone-beam computed tomography (CBCT) projection data acquired on a Varian TrueBeam linear accelerator. In these experiments, several CBCT scans were taken of an ICD lead placed in various orientations within a QUASAR respiratory motion phantom (Modus QA). The resulting projection images were exported (in XIM format). High-contrast regions corresponding to the metal ICD lead were contoured on the CBCT in the Eclipse™ treatment planning system. A DICOM Structure file containing the contour data was exported. For each kV projection image. The contour data was projected onto the image plane using the imaging system geometry provided in the exported XIM file. The bounding box for each target object was created by taking the minimum and maximum x and y values for the corresponding contour projection. The resulting region data was applied to train a neural network object detection model.

The described method facilitates quick creation of a large training dataset (images and regions of interest data) for the neural network model without having to manually annotate each CBCT projection image. 9055 images and their annotations were used to train and validate (80%/20% training/validation split) a Single Shot MultiBox Detector model using the TensorFlow™ Object Detection API. The model generates a bounding box for each detected instance of an object.

Metal regions of cardiac leads in test images were successfully detected using the trained model. The bounding boxes for each object could be used to track lead motion in the superior-inferior and lateral directions. The detector was capable of running at 30 frames per second on a GTX 1080 Ti GPU (33 ms detection time).

The model may be trained in a way general enough to reliably locate any of the most commonly implanted cardiac leads. In the alternative, to improve detection accuracy the trained model may be trained using images of the specific type of leads that are implanted in a patient to be treated. The training imaged could be acquired, for example using either a 4D CBCT or a number of limited-arc breath-hold scans of the patient.

Patient-specific training data may optionally be added to the existing neural network model to extend its detection capabilities.

Real time motions of cardiac leads determined by analyzing images of a patient and processing the images to recognize the cardiac leads may be further processed to obtain information regarding cyclical motions in the patient. For example, the motions of the cardiac leads may be processed to determine a period and phase of the patient's breathing and/or a period and phase of the patient's cardiac cycle.

Figure 6:
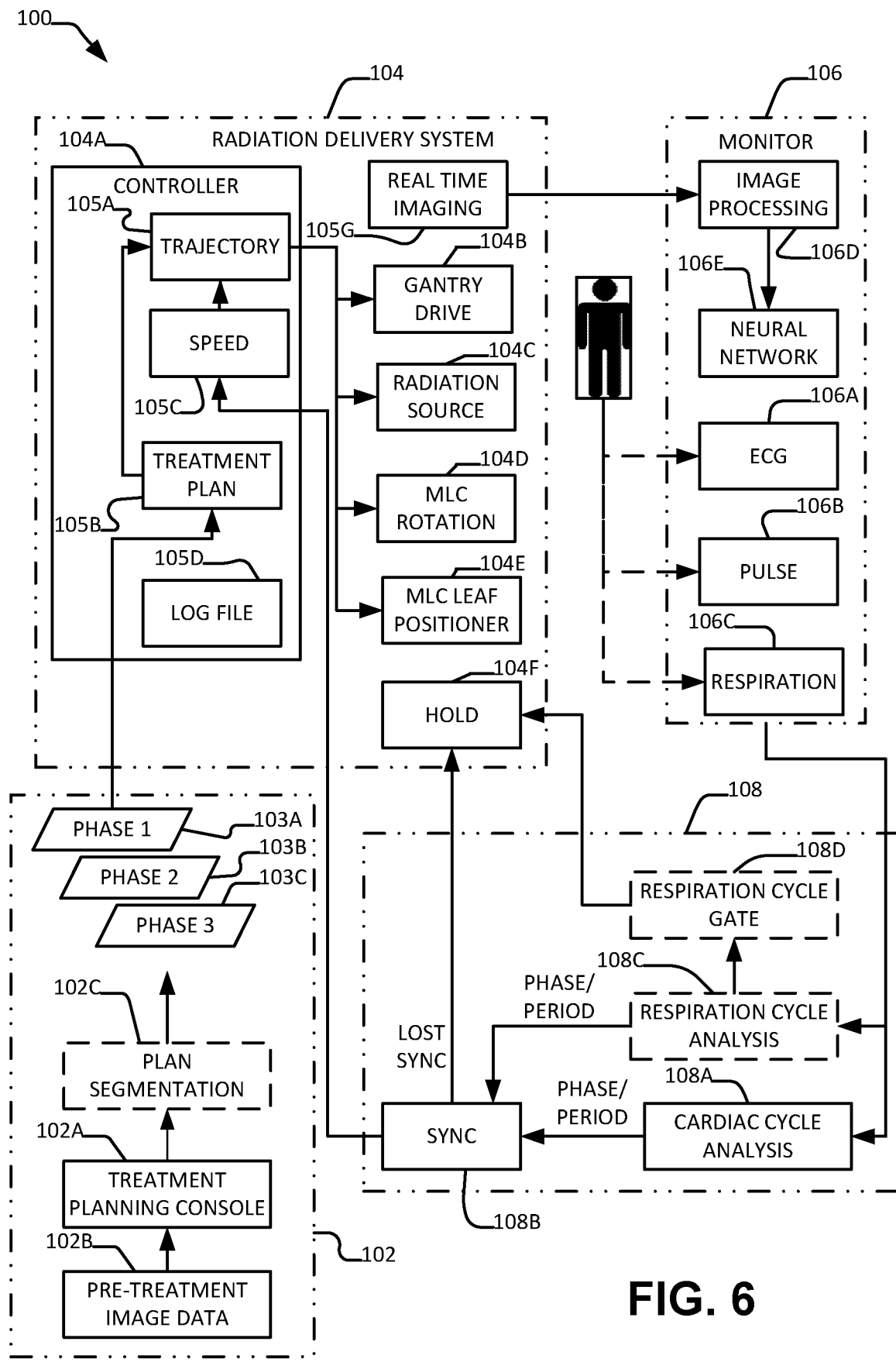
FIG. 6 is a block diagram illustrating apparatus according to an example embodiment.

FIG. 6 shows a radiation treatment system 100 according to an example embodiment. System 100 includes a radiation treatment planning part 102, a radiation delivery part 104, a patient monitoring part 106 and a synchronizing part 108. The division of system 100 into parts 102, 104, 106 and 108 is for convenience of explanation only. All of the illustrated parts may be integrated into a radiation delivery system or allocated in any suitable manner among plural units.

Radiation treatment planning part 102 is configured to generate radiation treatment plans as described herein. Radiation treatment planning part 102 includes a radiation treatment planning console 102A which is connected to receive pre-treatment planning images 102B. Images 102B may, for example, comprise computed tomography (CT) volumetric data. Console 102A may include a display and user interface controls which allow an operator to use functions of console 102A to generate a radiation treatment plan optimized for delivering a prescribed radiation dose to a patient and to check the radiation treatment plan.

A plan generated by console 102A is segmented by segmenting unit 102C, which outputs a segmented plan in which beam ON segments are allocated among a plurality of phases. In the illustrated embodiment phases 103A, 103B and 103C are produced.

In some embodiments the function of segmenting performed by segmenting unit 102C is integrated into console 102A, for example as a module which segments radiation treatment plans output by existing radiation treatment planning software or by providing in console 102A modified radiation treatment planning software which is configurable to output segmented radiation treatment plans without need for a further segmentation step.

Radiation delivery system 104 includes a controller 104A which is connected to control a radiation source 104C, a drive 104B which is connected to move radiation source 104C along a trajectory (e.g. a gantry drive which rotates a gantry carrying radiation source 104C in a selected arc) and actuators for controlling configuration of a beam shaper. In FIG. 7 controller 104A controls a MLC rotation drive 104E and an MLC leaf positioner 104F.

Controller 104A includes a trajectory controller 105A which coordinates operation of parts 104B to 104F to deliver a radiation treatment plan 105B. The speed with which the plan is executed is controlled by a speed control 105C. Speed control 105C is operative to increase or decrease the rate of travel of radiation source 104C along a trajectory and at the same time to increase or decrease the rate at which other machine components of radiation delivery system 104 are moved.

All movable machine components involved in delivery of radiation are slowed down or sped up simultaneously in proportion to maintain accurate dose delivery. For example, if the rate at which a gantry is being rotated is reduced from 100% of an initial speed to 50% of the initial speed then the rates at which a beam shaper is rotated, beam shaper components (e.g. leaves) are moved should also be reduced to 50% of their initial speeds. Also, the beam intensity should be cut to 50% of its initial beam intensity. Controller 104A may automatically control the intensity (fluence) of the radiation beam output by radiation source 104B in proportion to the speed set by speed control 105C.

To facilitate synchronizing the delivery of beam ON segments with quiescent periods the segmented radiation treatment plan may be developed to be deliverable with performance parameters of a radiation delivery system (e.g. dose rate, gantry speed and acceleration, Multi-leaf Collimator leaf speed and acceleration etc.) in a limited range within machine nominal and maximum values.

Monitor 106 may include one or more of the illustrated modalities for monitoring cycles in patient P. In the illustrated embodiment these include ECG system 106A, a pulse detector 106B, a respiration detector 106C and an image processing system 106D connected to process real time images obtained from an imaging system 105G associated with radiation delivery system 104.

Pulse detector 106B, if present, may detect heartbeat pulses by any suitable known technology including, for example any measuring optical or electrical properties of the patient or acceleration of a member placed to detect heartbeat or measuring heartbeat induced variations in the interaction between the patient and wireless electromagnetic signals (e.g. ultra wideband UWB signals) etc.

Respiration detector 106C, if present, may detect respiration in any suitable known technology including, detecting expansion of the patient's chest e.g. with a transducer belt, proximity sensor or camera, detecting air flow in a breathing tube, detecting respiration induced changes in impedance of the patient's body, detecting expansion of the patient's lungs with an imaging modality, respiratory inductive plethysmograph (RIP) technology, analysis of respiratory sounds, analysis of expelled air, analysis of ECG signals, using MRI to detect respiratory motion of the patient's diaphragm or other anatomical structure etc.

Imaging system 105G, if present, may comprise a MRI or CBCT or fluoroscopic or planar kV imaging system, for example. For example, a MRI system, which may be integrated with radiation delivery system 104, may generate a navigator which directly measures motions of a target volume of the radiation treatment or another tissue. The measured motion may result from one or both of cardiac and respiration movements, for example. A "navigator" is a measurement made by causing the MRI system to provide additional RF pulses which can be used to dynamically track anatomic motion. Navigator pulses may, for example be spin echo (SE) or gradient echo (GRE) pulses. MRI systems may be configured to include a graphical user interface which allows a user to select the region to be monitored by a navigator. A navigator can monitor motion of a band of tissue that is typically 1-2 cm wide with about 1-mm spatial resolution.

Synchronizing part 108 receives signals from monitoring part 106 and processes the signals to determine characteristics of one or more cycles (e.g. cardiac cycle and/or respiratory cycle) of patient P.

Cardiac cycle analysis 108A processes signals from monitor 106 to obtain information that indicates the period (T1) and phase (e.g. when will the next quiescent interval of the cardiac cycle of patient P start) of the patient's cardiac cycle.

The period and phase information is provided to sync unit 108B which determines in real time in coordination with controller 104A whether it is necessary to speed up or slow down delivery of radiation treatment plan 105B by radiation delivery system 104 so that the next beam ON segment of the segmented radiation treatment plan 105B will coincide with a quiescent interval of the patient's cardiac cycle. Sync unit 108B may obtain information regarding the current position and speed of radiation source 104B and the location of the start of the next beam ON segment from controller 104A and use this information in combination with the period and phase information to maintain/adjust synchronization. In some embodiments sync unit 108B is integrated with controller 104A.

Sync unit 108B provides control signals to speed control 105C which cause speed control 105C to make any needed adjustments to the speed of delivery by radiation delivery system 104.

If sync unit 108B determines that synchronization between the patient's cardiac cycle and the execution of treatment plan 105B cannot be maintained (e.g. if the patient's heart rate is higher than a threshold) then sync unit 108B may provide a HOLD signal to Hold input 104F of radiation treatment system 104 to cause radiation treatment system 104 to interrupt delivery of treatment plan 105B.

In the illustrated embodiment, synchronization part 108 includes respiration cycle analysis unit 108C which monitors the processes signals from monitor 106 to obtain information that indicates the period and phase (e.g. when will the next quiescent interval of the respiratory cycle of patient P start) of the patient's respiratory cycle.

If respiration cycle analysis 108C is present then it may deliver period and phase information for the patient's respiratory cycle to sync unit 108B which may operate to synchronize delivery of treatment plan 105B to coincide with quiescent intervals of the cardiac cycle that occur within quiescent intervals of the respiratory cycle.

As another option, if respiration cycle analysis 108C is present then it may control gating of delivery of radiation by way of respiration cycle gate 108D which generates and delivers a HOLD signal to hold input 104F when respiratory motion is causing the target volume(s) to be moving or to be displaced from the location at which the radiation beam is directed. Another option is to apply a target tracking technology that automatically steers the radiation beam to compensate for respiration induced motions of the target volume.

In some embodiments, radiation delivery system 104 includes features which track motion of a target volume that results from respiration of the patient and steer the radiation beam and/or control beam shaping to compensate for respiration-induced motion of the target volume. An example of a radiation delivery system that incorporates such functionality is the Vero™ linear accelerator available from Brainlab AG and Mitsubishi Heavy Industries Lt. of Japan. In cases where a radiation delivery system that has such a capability is used to deliver radiation it may not be necessary to perform gating or synchronization relative to the patient's respiratory cycle.

In some embodiments where a patient is equipped with a variable rate heart pacemaker the pacemaker may be controlled (e.g. by way of a programmer for the pacemaker) to set the patient's heart rate at a rate that is selected for delivery of segments of a radiation treatment plan as described herein. In some embodiments the patient's heart rate is controlled in real time to synchronize quiescent intervals of the cardiac cycle with delivery of beam ON segments.

Any parts of apparatus 100 that perform analysis or processing of any kind may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. All of these possibilities are encompassed within the term 'data processor'. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Data processing for functional elements of apparatus 100 that are illustrated by separate blocks in FIG. 6 may be implemented using different data processor or processing for two or more or all such functional elements may be implemented on the same data processor (e.g. by different software routines executing on a programmable processor). Similarly, data processing for any functional element or combination of functional elements of apparatus 100 may distributed in any suitable way among plural data processors.

In some embodiments radiation delivery system 104 includes a radiation blocking shutter that can be positioned to block the radiation beam or moved to allow the radiation beam to pass with a fast actuator. In such embodiments the beam is left ON during the delivery of a phase and the shutter is opened at the beginning of each beam ON segment and closed at the end of each beam ON segment. In such embodiments turning the beam ON and OFF (by blocking or unblocking the beam) may be close to instantaneous.

EXAMPLE 1

As a proof of concept a conventional VMAT plan was segmented to provide a three phase segmented plan (CSVMAT). The original VMAT plan and the CSVMAT plan synchronized to a synthesized cardiac signal were each delivered to a film phantom using a Varian™ TrueBeam™ linear accelerator.

For the proof of concept experiment a VMAT plan was optimized for delivery to a modified Quasar™ phantom (Modus Medical. A cylinder capable of accepting Gafchromic film was created from acrylic and inserted into the centre receptacle of the Quasar phantom to approximate the heart. A cedar wood insert was placed in the peripheral receptacle of the Quasar phantom to approximate lung.

A cylindrical planning target volume (PTV; diameter=4 cm, length=4.25 cm) was created and the lung insert was contoured as the lung. The plan was optimized to give a single fraction prescription dose of 400 cGy to 95% of the PTV, resulting in a maximum dose of 553.2 cGy. The plan was optimized for a 10 MV flattening filter-free mode employing a dose rate of 800 MU/min. The dose per fraction was chosen to provide an effective dose range for Gafchromic film measurement acknowledging that radiosurgery doses are often substantially higher.

The CSVMAT plan was created by running the original VMAT plan on the linear accelerator and then segmenting trajectory log files generated by the linear accelerator. The CSVMAT plan was presented in the form of XML files that could be read and delivered using Varian's TrueBeam developer mode—each XML file contains a list of sequential control points that the machine is instructed to follow, where each control point defines instantaneous machine parameters.

The particular linear accelerator used for the proof of concept experiment had several characteristics that needed to be worked around. These included:
1. the linear accelerator requires all plan parameters to be calculated prior to beam delivery. Real-time changes to the parameters during beam delivery are not supported;
2. the linear accelerator does not support direct control of beam timing. The linear accelerator delivers any plan as quickly as possible. The speed at which the linear accelerator progresses through the plan is determined by whichever machine parameter is the limiting factor.
3. the linear accelerator interprets motion-only segments with zero monitor units (MU) being delivered as beam holds. Each beam hold causes gantry motion to stop.

The first characteristic was worked around by adjusting timing parameters using only a priori ECG information.

The second characteristic was worked around by including in the plan specified motion for an otherwise unnecessary machine axis (in this case couch position) and setting a maximum speed for that unnecessary machine axis to a low value such that the rate at which the linear accelerator executed a plan was limited by the rate at which the unnecessary machine axis was permitted to move. Time between one control point and the next control point could be increased by specifying greater movement for the unnecessary axis between the control points or decreased by specifying a shorter distance of couch motion between the control points.

In the proof of concept experiment the couch maximum velocity was set to 1 cm per second so that couch movement was forced to be the limiting factor. By programming the couch to move a certain distance between adjacent control points it is possible to adjust the time it takes to deliver each plan segment.

For example, setting the couch to move 2 cm between two control points at a speed of 1 cm per second will force that segment of the plan to take a total of 2 seconds. The control system of the linear accelerator automatically adjusts speeds of all moving linear accelerator components to maintain the proper dose delivery. Thus, increasing couch movement slows down beam delivery (for a slower heart rate), while decreasing couch movement speeds up beam delivery (for a faster heart rate).

To avoid alteration of the distribution of radiation as a result of the couch motion, the phantom was placed on top of a stationary custom table which allowed the couch to move while the phantom stayed still.

The third characteristic was addressed by specifying for beam OFF portions an negligible radiation delivery (0.001 MU) instead of zero radiation delivery.

The VMAT base plan and the interleaved synchronized plans were each delivered to the phantom using a True-Beam™ linear accelerator. The dose distribution delivered by each plan was measured using Gafchromic EBT3 film. The films were scanned on an Epson Expression 10000XL scanner and converted to dose using FilmQA Pro software (Ashland Advanced Materials). The delivered dose distributions from the base and the interleaved synchronized plans were compared with each other. A gamma analysis was also performed between the original VMAT plan and the CSVMAT version using the FilmQA Pro software. Trajectory logs were also obtained for each beam delivery. Measurements of gantry position, monitor unit index (a radiation fluence metric) and multileaf collimator (MLC) leaf positions were extracted from the trajectory log files.

Figure 5:
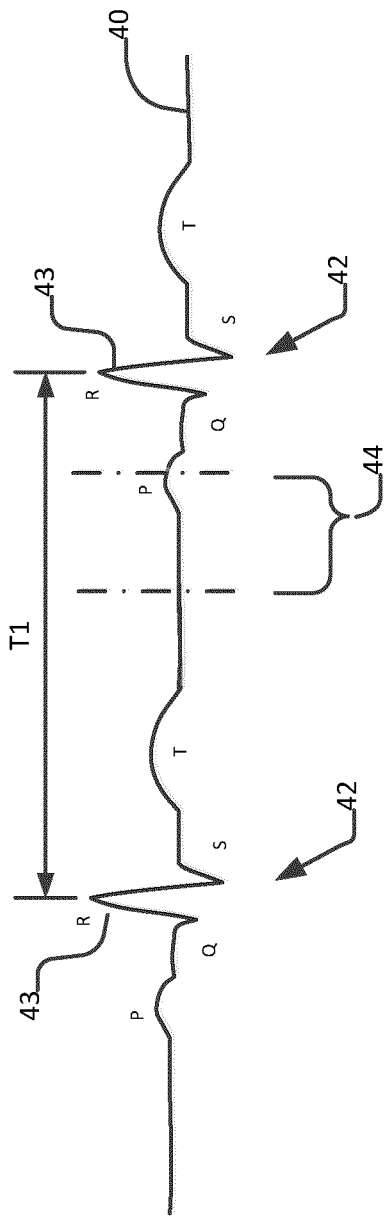
FIG. 5 is a plot showing an ECG signal for the case where heart rate is increasing with a superposed plot of radiation intensity.
Figure 5:
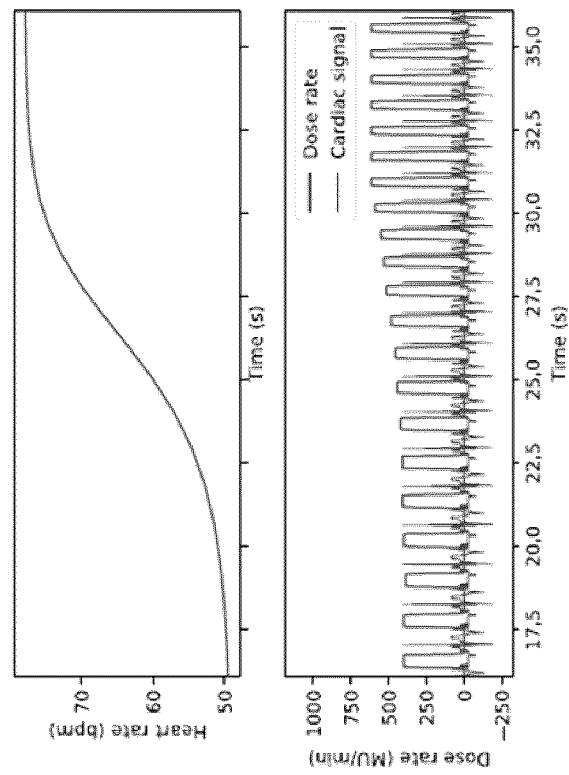

The trajectory log file for one of the three phases of the CSVMAT plan is shown in FIG. 5. In the example, the heart rate was changed between 49 and 78 beats bpm during delivery (FIG. 5—top). To maintain synchronization, the linear accelerator control system adjusts all of the required machine parameters according to the limiting axis (couch movement). As the heart rate increases (cardiac period decreases), the dose rate, gantry speed, and MLC leaf speed increase to shorten the arc segment durations. In FIG. 5 (bottom) the change in dose rate can be seen to increase allowing for the same integral dose to be delivered over the shorter cardiac cycle. Analysis of trajectory logs from the linear accelerator showed successful synchronization of the CSVMAT plan with the a priori cardiac signal.

The gantry rotation was also relatively smooth throughout the beam delivery. In the example, the average absolute gantry acceleration was 0.115 deg/s$^2$ By keeping the gantry moving between beam ON and beam OFF periods in each phase, the total time to deliver each phase is reduced.

FIG. 7A shows FilmQA Pro dose isolines and FIG. 7B shows dose profile comparing the original VMAT treatment plan and the CSVMAT plan. A gamma passing rate of 99.4% was calculated for a 2%/2 mm tolerance.

The film measurement indicated that treating the VMAT plan using the cardiac synchronized technique has minimal impact on the delivered dose. In the tested case both the isodose maps (FIG. 7A) and the profile (FIG. 7B) show good agreement. Gamma analysis showed a passing rate of 99.4% was given (2%/2 mm tolerance), indicating excellent agreement between the interleaved cardiac-synchronized phases and the original treatment.

Methods of Medical Treatment

Some aspects of the invention provide methods of medical treatment wherein radiation is delivered to a patient for a therapeutic purpose. Exemplary embodiments of some such aspects of the invention are provided in the following enumerated example embodiments.

1. A method for delivering radiation to a subject, the method comprising:
   continuously moving a radiation source relative to the subject along a trajectory;
   operating the radiation source to deliver radiation in beam ON segments of the trajectory and controlling the radiation source to deliver no or negligible radiation in each of the a plurality of beam OFF portions of the trajectory;
   monitoring a cardiac cycle of the subject and determining from the cardiac cycle an estimated time for a next quiescent period of the cardiac cycle; and
   controlling a speed at which the radiation source is advanced along the trajectory to cause a next one of the beam ON segments to coincide with the next one of the quiescent periods.

2. The method of enumerated embodiment 1, wherein monitoring a cardiac cycle of the subject and determining from the cardiac cycle an estimated time for a next quiescent period of the cardiac cycle comprises:
   receiving an electrocardiogram (ECG) trace;
   processing the ECG trace to identify points where a rate of change of the ECG trace exceeds a threshold;
      locating within a window around each of the identified points of the ECG trace an R peak as a maximum of the ECG trace within the window;
      determining a time difference between two most recent adjacent R peaks as a period of a cardiac signal;
      locating between the two most recent adjacent R peaks a time of a most recent quiescent period; and
      estimating a time for a next quiescent period from the time difference and the time of the most recent quiescent period.

3. The method of enumerated embodiment 1, wherein monitoring a cardiac cycle of the subject and determining from the cardiac cycle an estimated time for a next quiescent period of the cardiac cycle comprises:
   receiving an electrocardiogram (ECG) trace;
   processing the ECG trace to identify points where a rate of change of the ECG trace exceeds a threshold;

locating within a window around each of the identified points of the ECG trace an R peak as a maximum of the ECG trace within the window;
determining a first time difference between first and second most recent adjacent R peaks as a first period of a cardiac signal;
determining a second time difference between second and third most recent adjacent R peaks as a second period of a cardiac signal;
locating between the two most recent adjacent R peaks a time of a most recent quiescent period; and
estimating a time for a next quiescent period from the first and second time differences and the time of the most recent quiescent period.

4. The method of enumerated embodiment 3, wherein monitoring a cardiac cycle of the subject and determining from the cardiac cycle an estimated time for a next quiescent period of the cardiac cycle comprises:
determining an nth time difference between the nth and n+1-th most recent adjacent R peaks as an nth period of a cardiac signal; and
estimating a time for a next quiescent period from the first, second through nth time differences and the time of the most recent quiescent period.

5. The method according to any one of enumerated embodiments 1-4, wherein each of the beam OFF portions of the trajectory is about twice as long as each of the beam ON segments of the trajectory.

6. The method according to any one of enumerated embodiments 1-5 wherein:
the radiation source is controlled according to a radiation treatment plan;
the radiation treatment plan comprises a plurality of phases;
each of the phases specifies a plurality of the beam ON segments of the trajectory and a plurality of the beam OFF portions of the trajectory; and
the beam ON segments in different ones of the phases are at different locations along the trajectory.

7. The method according to enumerated embodiment 6 wherein the beam ON segments in the different phases do not overlap with one another.

8. The method according to enumerated embodiment 6 wherein the radiation source has a ramp-up time and a ramp-down time during each beam ON segment, and beam ON segments in the different phases overlap so that for each beam ON segment a ramp-up time of that beam ON segment coincides with a ramp-down time of a different beam ON segment.

9. The method according to any one of enumerated embodiments 6-8 wherein the plurality of phases comprises three phases and the beam ON segments from all of the three phases collectively cover the entire trajectory.

10. The method according to any one of enumerated embodiments 1-9 wherein controlling a speed at which the radiation source is advanced along the trajectory comprises maintaining an average acceleration of the gantry to not exceed 0.15 deg/s$^2$ between a start of a first beam ON segment in the trajectory and the end of a last beam ON segment in the trajectory.

11. The method according to any one of enumerated embodiments 1-10, the method comprising:
controlling a speed with which a variable beam shaper is varied among configurations to match a speed at which the radiation source is advanced along the trajectory.

12. The method according to any one of enumerated embodiments 1-11 wherein the beam ON segments have lengths such that each beam ON segment can be delivered in a time not exceeding about 200 ms at a speed that does not exceed a maximum speed at which the drive can advance the radiation source along the trajectory.

13. The method according to any one of enumerated embodiments 1-12 comprising:
receiving images from a real time imaging system to locate a metallic lead in the images;
wherein monitoring a cardiac cycle of the subject and determining from the cardiac cycle an estimated time for a next quiescent period of the cardiac cycle comprises detecting cyclical motion of the metallic lead.

14. The method according to any one of enumerated embodiments 1-13 comprising:
controlling a beam intensity of the radiation source to match a rate at which the speed at which the radiation source is advanced along the trajectory.

15. The method according to enumerated embodiment 14 wherein controlling a beam intensity comprises modifying the beam intensity so that radiation flux through an angle swept by the radiation source during beam ON segments is maintained at a near constant value.

16. The method according to any one of enumerated embodiments 1-15 comprising:
pausing delivery of radiation to the subject if it is not possible to maintain synchronization of the delivery of radiation with quiescent periods of the cardiac cycle.

17. The method according to enumerated embodiment 16 wherein pausing delivery of radiation to the subject if it is not possible to maintain synchronization of the delivery of radiation with quiescent periods of the cardiac cycle is determined by a measurement of a reduction of a fidelity with which the delivery of radiation achieves a prescribed dose.

18. The method according to any one of enumerated embodiments 1-17 comprising:
varying a size of one or more beam ON segments and beam OFF portions in response to a change in the cardiac cycle.

19. A method for delivering radiation to a subject, the method comprising:
parametrizing a trajectory of a radiation source delivering a radiation beam to irradiate a target volume in a subject, subject to the constraint that the radiation beam is ON only for beam ON segments of the trajectory and is OFF in beam OFF portions of the trajectory between adjacent ones of the beam ON segments;
moving the radiation source relative to the subject during both beam ON segments and beam OFF portions along the trajectory; and
operating the radiation source to deliver radiation in beam ON segments of the trajectory and controlling the radiation source to deliver no or negligible radiation in each of a plurality of the beam OFF portions of the trajectory.

20. The method according to enumerated embodiment 19, wherein parametrizing a trajectory of a radiation source delivering a radiation beam to irradiate a target volume in a subject comprises:
receiving an electrocardiogram (ECG) trace;
identifying quiescent periods from the ECG trace; and
parameterizing the trajectory of the radiation source so that beam ON segments coincide with projected quiescent periods.

21. The method of enumerated embodiment 20, comprising:

monitoring a cardiac cycle of the subject and determining from the cardiac cycle an estimated time for a next quiescent period of the cardiac cycle; and controlling a speed at which the radiation source is advanced along the trajectory to cause a next one of the beam ON segments to coincide with the next one of the quiescent periods.

22. The method of enumerated embodiment 21, wherein monitoring a cardiac cycle of the subject and determining from the cardiac cycle an estimated time for a next quiescent period of the cardiac cycle comprises:

processing the ECG trace to identify points where a rate of change of the ECG trace exceeds a threshold;

locating within a window around each of the identified points of the ECG trace an R peak as a maximum of the ECG trace within the window; and determining a time difference between two most recent adjacent R peaks as a period of a cardiac signal;

designating a duration that is a first fraction of the period of the cardiac signal and starting a second fraction after each R peak as a quiescent period.

23. The method of enumerated embodiment 22, wherein the first fraction and the second fraction are each about one third.

24. The method according to any one of enumerated embodiments 19-23 wherein:

the radiation source is controlled according to a radiation treatment plan;

the radiation treatment plan comprises a plurality of phases;

each of the phases specifies a plurality of the beam ON segments of the trajectory and a plurality of the beam OFF portions of the trajectory; and the beam ON segments in different ones of the phases are at different locations along the trajectory.

25. The method according to enumerated embodiment 24 wherein the beam ON segments in the different phases do not overlap with one another.

26. The method according to enumerated embodiment 24 wherein the radiation source has a ramp-up time and a ramp-down time during each beam ON segment, and beam ON segments in the different phases overlap so that for each beam ON segment a ramp-up time of that beam ON segment coincides with a ramp-down time of a different beam ON segment.

27. The method according to any one of enumerated embodiments 24-26 wherein the plurality of phases comprises three phases and the beam ON segments from all of the three phases collectively cover the entire trajectory.

28. The method according to any one of enumerated embodiments 19-27 wherein parametrizing a trajectory of a radiation source delivering a radiation beam to irradiate a target volume in a subject comprises:

specifying configurations of a variable beam shaper at least for points along the trajectory in the beam ON segments; and adjusting a speed with which the variable beam shaper is varied among the configurations to match the speed at which the radiation source is advanced along the trajectory.

29. The method according to any one of enumerated embodiments 19-28 wherein the beam ON segments have lengths such that each beam ON segment can be delivered in a time not exceeding about 200 ms at a speed that does not exceed a maximum speed at which the drive can advance the radiation source along the trajectory.

30. The method according to enumerated embodiment 24 further comprising:

specifying the target volume for the radiation treatment plan; and generating the radiation treatment plan based at least in part on the specified target volume.

31. The method according to any one of enumerated embodiments 19-30 wherein parametrizing a trajectory of a radiation source delivering a radiation beam to irradiate a target volume in a subject comprises:

receiving a preliminary radiation treatment plan; and segmenting the preliminary radiation treatment plan to provide beam ON segments and beam OFF portions.

32. The method of enumerated embodiment 21, wherein monitoring a cardiac cycle of the subject and determining from the cardiac cycle an estimated time for a next quiescent period of the cardiac cycle comprises:

receiving an electrocardiogram (ECG) trace;

processing the ECG trace to identify points where a rate of change of the ECG trace exceeds a threshold;

locating within a window around each of the identified points of the ECG trace an R peak as a maximum of the ECG trace within the window;

determining a time difference between two most recent adjacent R peaks as a period of a cardiac signal;

locating between the two most recent adjacent R peaks a time of a most recent quiescent period; and estimating a time for a next quiescent period from the time difference and the time of the most recent quiescent period.

33. The method of enumerated embodiment 21, wherein monitoring a cardiac cycle of the patient and determining from the cardiac cycle an estimated time for a next quiescent period of the cardiac cycle comprises:

receiving an electrocardiogram (ECG) trace;

processing the ECG trace to identify points where a rate of change of the ECG trace exceeds a threshold;

locating within a window around each of the identified points of the ECG trace an R peak as a maximum of the ECG trace within the window;

determining a first time difference between first and second most recent adjacent R peaks as a first period of a cardiac signal;

determining a second time difference between second and third most recent adjacent R peaks as a second period of a cardiac signal;

locating between the two most recent adjacent R peaks a time of a most recent quiescent period; and estimating a time for a next quiescent period from the first and second time differences and the time of the most recent quiescent period.

34. The method of enumerated embodiment 33, wherein monitoring a cardiac cycle of the patient and determining from the cardiac cycle an estimated time for a next quiescent period of the cardiac cycle comprises:

determining an nth time difference between the nth and n+1-th most recent adjacent R peaks as an nth period of a cardiac signal; and estimating a time for a next quiescent period from the first, second through nth time differences and the time of the most recent quiescent period.

35. The method according to any one of enumerated embodiments 19-34, wherein each of the beam OFF portions of the trajectory is about twice as long as each of the beam ON segments of the trajectory.

36. The method according to any one of enumerated embodiments 19-35 wherein controlling a speed at which the radiation source is advanced along the trajectory comprises maintaining an average acceleration of the gantry to not exceed 0.15 deg/s$^2$ between a start of a first beam ON segment in the trajectory and the end of a last beam ON segment in the trajectory.

37. The method according to any one of enumerated embodiments 19-36 comprising:
receiving images from a real time imaging system to locate a metallic lead in the images;
wherein monitoring a cardiac cycle of the patient and determining from the cardiac cycle an estimated time for a next quiescent period of the cardiac cycle comprises detecting cyclical motion of the metallic lead.

38. The method according to any one of enumerated embodiments 19-37 comprising:
controlling a beam intensity of the radiation source to match a rate at which the speed at which the radiation source is advanced along the trajectory.

39. The method according to enumerated embodiment 38 wherein controlling a beam intensity comprises modifying the beam intensity so that radiation flux through an angle swept by the radiation source during beam ON segments is maintained at a near constant value.

40. The method according to any one of enumerated embodiment 19-39 comprising:
pausing delivery of radiation to the subject if it is not possible to maintain synchronization of the delivery of radiation with quiescent periods of the cardiac cycle.

41. The method according to enumerated embodiment 40 wherein pausing delivery of radiation to the subject if it is not possible to maintain synchronization of the delivery of radiation with quiescent periods of the cardiac cycle is determined by a measurement of a reduction of a fidelity with which the delivery of radiation achieves a prescribed dose.

42. The method according to any one of enumerated embodiments 19-41 comprising:
varying a size of one or more beam ON segments and/or beam OFF portions in response to a change in the cardiac cycle.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

Where processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times and/or in different sequences.

Some aspects of the invention may be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. a software module, processor, drive, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An apparatus for delivering a radiation treatment to a patient, the apparatus comprising:
   a radiation source;
   a drive connected to move the radiation source along a trajectory relative to the patient;
   a memory having stored therein a radiation treatment plan specifying a plurality of beam ON segments of the trajectory and specifying a plurality of beam OFF portions of the trajectory interleaved with the plurality of beam ON segments of the trajectory;
   a patient monitoring system connected to monitor a cardiac cycle of the patient, wherein the cardiac cycle includes quiescent periods;
   one or more data processors connected to:
      control the drive to advance the radiation source along the trajectory;
      control the radiation source to deliver radiation in each of the plurality of beam ON segments of the trajectory and to deliver no or negligible radiation in each of the plurality of beam OFF portions of the trajectory;
      process an output of the patient monitoring system to estimate a time for a next one of the quiescent periods of the cardiac cycle; and
      control a speed at which the radiation source is advanced along the trajectory to cause a next one of the plurality of beam ON segments to coincide with the next one of the quiescent periods of the cardiac cycle.

2. The apparatus according to claim 1, wherein the patient monitoring system comprises an electrocardiogram (ECG) system.

3. The apparatus according to claim 2, wherein the one or more data processors are configured to:
   receive an ECG trace from the patient monitoring system;
   process the ECG trace to identify points, where a rate of change of the ECG trace exceeds a threshold;
   within a window around each of the identified points of the ECG trace locate an R peak as a maximum of the ECG trace within the window;
   determine a time difference between two most recent adjacent R peaks as a period of the cardiac signal and determine the estimated time for a next one of the quiescent periods based on the determined time difference between the two most recent adjacent R peaks.

4. The apparatus according to claim 1, wherein the patient monitoring system comprises one or more of: a real-time imager; a pulse monitor; or an impedance-based monitor.

5. The apparatus according to claim 1, wherein the patient monitoring system comprises a real-time imager, the apparatus further comprising an image processor that includes a model trained to locate metallic cardiac leads in images obtained by the real-time imager and to process locations of the metallic cardiac leads determined by the model to determine motions of the metallic cardiac leads.

6. The apparatus according to claim 1, wherein each of the plurality of beam OFF portions of the trajectory is about twice as long as each of the plurality of beam ON segments of the trajectory.

7. The apparatus according to claim 1, wherein:
   the radiation treatment plan comprises a plurality of phases;
   the one or more data processors are configured to execute the plurality of phases in a sequence;
   each of the plurality of phases specifies a subset of the plurality of beam ON segments of the trajectory and a subset of the plurality of beam OFF portions of the trajectory; and
   subsets of the plurality of beam ON segments in different ones of the plurality of phases are at different locations along the trajectory.

8. The apparatus according to claim 7, wherein subsets of the plurality of beam ON segments in different phases overlap by a length corresponding to a ramp up time for the radiation source.

9. The apparatus according to claim 7, wherein the plurality of phases comprises three phases, and subsets of the plurality of beam ON segments from the three phases collectively cover the trajectory.

10. The apparatus according to claim 1, further comprising:
    a data store connected to record the output of the patient monitoring system, wherein:
       the one or more data processors are configured to process the output of the patient monitoring system to estimate a time for a next one of the quiescent periods by processing most recent data in the data store; and
       the one or more data processors are configured to determine a cardiac cycle period from the most recent data in the data store, and to estimate the time for a next one of the quiescent periods based in part on the determined cardiac cycle period; or
       the one or more data processors are configured to determine a time derivative of a cardiac cycle period from the most recent data in the data store, and to estimate the time for a next one of the quiescent periods based in part on the determined time derivative of the cardiac cycle period.

11. The apparatus according to claim 1, wherein the one or more data processors are configured to advance the radiation source along the trajectory without stopping until at least the end of a last one of the plurality of beam ON segments.

12. The apparatus according to claim 1, further comprising:
    a gantry,
    wherein the radiation source is mounted to the gantry which is rotatable about an axis, the trajectory comprises an arc made by the radiation source as the gantry is rotated between a starting angle and an ending angle, and the one or more data processors are configured to maintain an average acceleration of the gantry to not exceed 0.15 deg/s² between a start of a first beam ON segment in the trajectory and the end of a last beam ON segment in the trajectory.

13. The apparatus according to claim 1, further comprising:
a variable beam shaper,
wherein the radiation treatment plan comprises parameters specifying configurations of the variable beam shaper at least for points along the trajectory in the plurality of beam ON segments, and the one or more data processors are configured to adjust a speed with which the variable beam shaper is varied among the configurations to match the speed at which the radiation source is advanced along the trajectory.

14. The apparatus according to claim 1, wherein the plurality of beam ON segments have lengths such that each beam ON segment can be delivered in a time not exceeding about 200 ms at a speed that does not exceed a maximum speed at which the drive can advance the radiation source along the trajectory.

15. The apparatus according to claim 1, wherein the one or more data processors are configured to receive a preliminary radiation treatment plan, and to segment the preliminary radiation treatment plan to provide the radiation treatment plan.

16. A method for controlling a position of a radiation source of a radiation delivery system along a trajectory, the method comprising:
reading a radiation treatment plan specifying locations along the trajectory of a plurality of beam ON segments and a plurality of beam OFF portions interleaved between the plurality of beam ON segments;
processing an output of a patient monitoring system configured to monitor a cardiac cycle of the patient to estimate a starting time for starting a next one of the plurality of beam ON segments such that the next one of the plurality of beam ON segments will coincide with a quiescent period of the cardiac cycle; and
adjusting a speed at which the radiation source is being driven along the trajectory to cause the radiation source to arrive at a location along the trajectory corresponding to the next one of the plurality of beam ON segments at the starting time.

17. The method according to claim 16, wherein the output of the patient monitoring system comprises an electrocardiogram (ECG) trace, and the method further comprises:
processing the ECG trace to identify points, where a rate of change of the ECG trace exceeds a threshold;
locating within a window around each of the identified points of the ECG trace an R peak as a maximum of the ECG trace within the window;
determining a time difference between two most recent adjacent R peaks as a period of a cardiac signal; and
designating a duration that is a first fraction of the period of the cardiac signal, and starting a second fraction after each R peak as a quiescent period.

18. The method of claim 17, wherein the first fraction and the second fraction are each about one third.

19. The method according to claim 16, further comprising determining a specified configuration for a variable beam shaper specified by the radiation treatment plan for a start of the next one of the plurality of beam ON segments, and driving elements of the variable beam shaper at constant speeds selected to cause the variable beam shaper to have the specified configuration at the starting time.

20. The method according to claim 16, further comprising updating the starting time, and adjusting the speed at which the radiation source is being driven along the trajectory according to the updated starting time.

21. A method for delivering radiation to a patient, the method comprising:
providing a radiation delivery system comprising a radiation source moveable along a trajectory;
receiving a radiation treatment plan specifying locations along the trajectory of a plurality of beam ON segments and a plurality of beam OFF portions interleaved between the plurality of beam ON segments;
monitoring a cardiac cycle of the patient to determine a plurality of quiescent periods of the cardiac cycle;
controlling a speed at which the radiation source is moved along the trajectory based on the cardiac cycle, and adjusting the speed at which the radiation source is moved along the trajectory in response to changes in a period of the cardiac cycle, such that a time at which the radiation source reaches each of the specified locations of the plurality of beam ON segments coincides with one of the plurality of quiescent periods of the cardiac cycle; and
controlling the radiation source to deliver radiation in each of the plurality of beam ON segments of the trajectory and to deliver no or negligible radiation in each of the plurality of beam OFF portions of the trajectory.

* * * * *